(12) United States Patent
Chu et al.

(10) Patent No.: US 8,729,104 B2
(45) Date of Patent: May 20, 2014

(54) DIPHENYL SUBSTITUTED ALKANES AS FLAP INHIBITORS

(75) Inventors: Lin Chu, Scotch Plains, NJ (US); Ihor E. Kopka, Hampton, NJ (US); Bing Li, Towaco, NJ (US); Anthony K. Ogawa, Mountainside, NJ (US); Feroze Ujjainwalla, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 370 days.

(21) Appl. No.: 13/021,992

(22) Filed: Feb. 7, 2011

(65) Prior Publication Data

US 2011/0190346 A1  Aug. 4, 2011

Related U.S. Application Data

(63) Continuation of application No. 11/665,242, filed as application No. PCT/US2005/036940 on Oct. 14, 2005, now abandoned.

(60) Provisional application No. 60/619,752, filed on Oct. 18, 2004.

(51) Int. Cl.
*A61K 31/4439* (2006.01)
*C07D 413/12* (2006.01)

(52) U.S. Cl.
USPC ........................ 514/340; 546/269.1

(58) Field of Classification Search
USPC ........................ 546/269.1; 514/340
See application file for complete search history.

(56) References Cited

U.S. PATENT DOCUMENTS

| 4,853,398 A | 8/1989 | Carr et al. |
| 5,795,900 A | 8/1998 | Brooks et al. |
| 2006/0211677 A1 | 9/2006 | Chu et al. |

FOREIGN PATENT DOCUMENTS

WO  WO 2006098912 A1  9/2006

OTHER PUBLICATIONS

Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burgers Medicinal Chemistry and Drug Discovery. 5th ed. vol. 1: Principles and Practice. pp. 949-982.*
Guillory (in Brittain ed.), "Polymorphism in Pharmaceutical Solids.," NY: Marcel Dekker, Inc., 1999, 1-2, 125-181, 183-226.*
Yu et al., "Physical characterization of, etc.," PSTT, vl. 1(3), 118-127 (1998).*
Vippagunta et al., "Crystalline Solids", Advanced Drug Delivery Reviews 48 (2001) 3-26.*
Charleston, S. et al., "Characterization of a 5-Lipoxygenase-Activating Protein Binding Assay: Correlation of Affinity for 5-Lipoxygenase-Activating Protein with Leukotrine Synthesis Inhibition", Molecular Pharmacology, vol. 41, pp. 873-879, 1992.

* cited by examiner

*Primary Examiner* — Patricia L Morris
(74) *Attorney, Agent, or Firm* — Maria V. Marucci; Valerie J. Camara

(57) ABSTRACT

The instant invention provides compounds of formula I which are 5-lipoxygenase activating protein inhibitors.

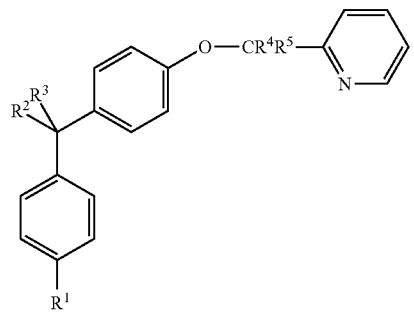

Compounds of formula I are useful as anti-atherosclerotic, anti-asthmatic, anti-allergic, anti-inflammatory and cytoprotective agents.

9 Claims, 6 Drawing Sheets

DIPHENYL SUBSTITUTED ALKANES AS FLAP INHIBITORS

FIELD OF THE INVENTION

The instant invention involves compounds that inhibit 5-lipoxygenase activating protein (FLAP), compositions containing such compounds and methods of treatment using such compounds for the treatment and prevention of atherosclerosis and related diseases and conditions.

BACKGROUND OF THE INVENTION

Inhibition of leukotriene biosynthesis has been an active area of pharmaceutical research for many years. Leukotrienes are potent contractile and inflammatory mediators derived through the oxygenation of arachidonic acid by 5-lipoxygenase.

One class of leukotriene biosynthesis inhibitors are those known to act through inhibition of 5-lipoxygenase (5-LO). In general, 5-LO inhibitors have been sought for the treatment of allergic rhinitis, asthma and inflammatory conditions including arthritis. One example of a 5-LO inhibitor is the marketed drug zileuton, which is indicated for the treatment of asthma. More recently, it has been reported that 5-LO may be an important contributor to the atherogenic process; see Mehrabian, M. et al., Circulation Research, 2002 Jul. 26, 91(2):120-126.

A new class of leukotriene biosynthesis inhibitors (now known as FLAP inhibitors) distinct from 5-LO inhibitors is described in Miller, D. K. et al., "Identification and isolation of a membrane protein necessary for leukotriene production," Nature, vol. 343, No. 6255, pp. 278-281(18 Jan. 1990). See also Dixon, R. A. et al, "Requirement of a 5-lipoxygenase-activating protein for leukotriene synthesis," Nature, vol 343, no. 6255, pp. 282-4 (18 Jan. 1990). 5-LO inhibitor compounds were used to identify and isolate the inner nuclear membrane 18,000 dalton protein 5-lipoxygenase-activating protein (FLAP). These compounds inhibit the formation of cellular leukotrienes but have no direct effect on soluble 5-LO activity. In cells, arachidonic acid is released from membrane phospholipids by the action of cytosolic phospholipase 2. This arachidonic acid is transferred to nuclear membrane bound 5-lipoxygenase by FLAP. The presence of FLAP in cells is essential for the synthesis of leukotrienes. Additionally, based on studies described in Helgadottir, A., et al., Nature Genetics, vol 36, no. 3 (March 2004) pp. 233-239, it is believed that the gene encoding 5-lipoxygenase activating protein confers risk for myocardial infarction and stroke in humans.

Despite significant therapeutic advances in the treatment and prevention of atherosclerosis and ensuing atherosclerotic disease events, such as the improvements that have been achieved with HMG-CoA reductase inhibitors, further treatment options are clearly needed. The instant invention addresses that need by providing compounds, compositions and methods for the treatment or prevention of atherosclerosis as well as related conditions.

SUMMARY OF THE INVENTION

The instant invention relates to compounds of formula I which are FLAP inhibitors, methods for their preparation, and methods and pharmaceutical formulations for using these compounds in mammals, especially humans. This invention provides compounds of structural formula I:

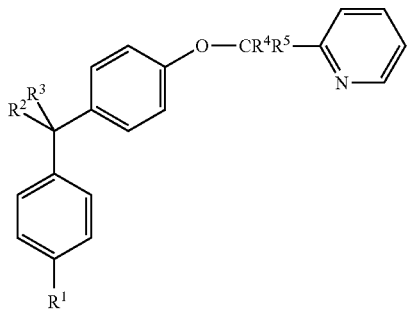

and the pharmaceutically acceptable salts, esters and solvates thereof. This invention also involves the use of compounds described herein to slow or halt atherogenesis. Therefore, one object of the instant invention is to provide a method for treating atherosclerosis, which includes halting or slowing the progression of atherosclerotic disease once it has become clinically evident, comprising administering a therapeutically effective amount of a compound of formula I to a patient in need of such treatment. Another object is to provide methods for preventing or reducing the risk of developing atherosclerosis and atherosclerotic disease events, comprising administering a prophylactically effective amount of a compound of Formula I to a patient who is at risk of developing atherosclerosis or having an atherosclerotic disease event.

The compounds of Formula I are also useful as anti-asthmatic, anti-allergic, anti-inflammatory and cytoprotective agents. They are also useful in treating angina, cerebral spasm, glomerular nephritis, hepatitis, endotoxemia, uveitis, and allograft rejection. The instant invention provides methods of treatment comprising administering a therapeutically effective amount of a compound of Formula I to a patient in need of the above-described treatments.

A further object is to provide the use of FLAP inhibitors of formula I in combination with other therapeutically effective agents, including other anti-atherosclerotic drugs. These and other objects will be evident from the description contained herein.

BRIEF DESCRIPTION OF THE DRAWINGS

FIG. 1 is an X-ray powder diffraction pattern observed for crystalline Form I of compound 1a.

FIG. 2 is a differential scanning calorimetry curve for crystalline Form I of compound 1a.

FIG. 3 is an X-ray powder diffraction pattern observed for crystalline Form II of compound 1a.

FIG. 4 is a differential scanning calorimetry curve for crystalline Form II of compound 1a.

FIG. 5 is a carbon-13 cross-polarization magic-angle spinning (CPMAS) nuclear magnetic resonance (NMR) spectrum of the crystalline Form I of compound 1a.

FIG. 6 is a carbon-13 cross-polarization magic-angle spinning (CPMAS) nuclear magnetic resonance (NMR) spectrum of the crystalline Form II of compound 1a.

DETAILED DESCRIPTION OF THE INVENTION

Figure 1:
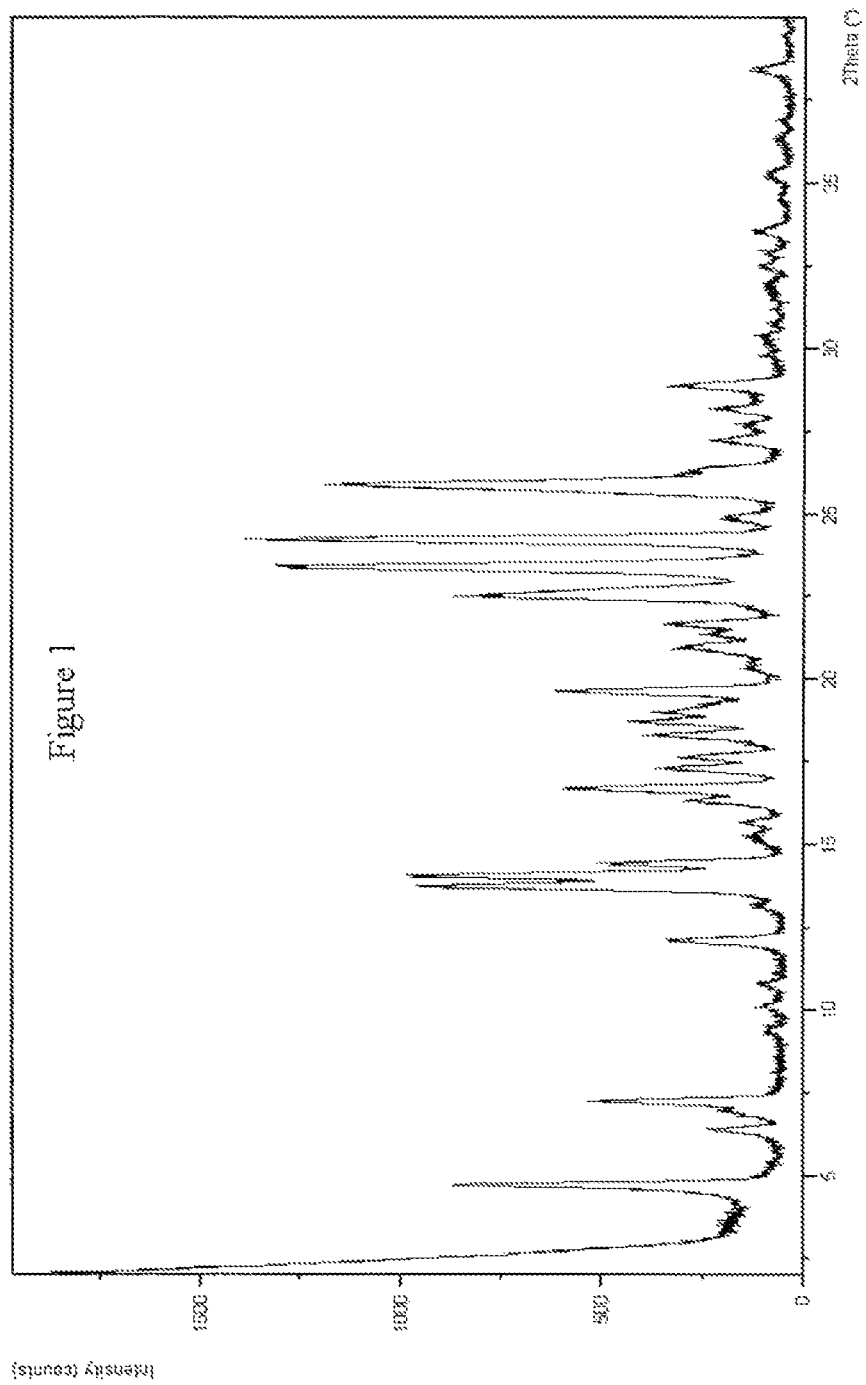

The instant invention provides a compound represented by structural formula I

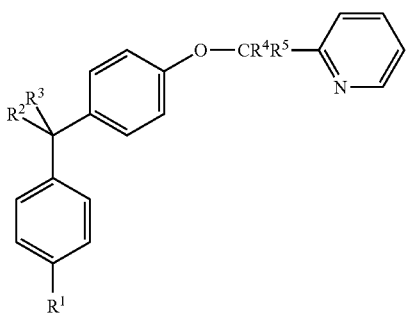

the pyridyl-N-oxide analog of formula I, and the pharmaceutically acceptable salts, esters and solvates thereof wherein:

$R^1$ is selected from the group consisting of:

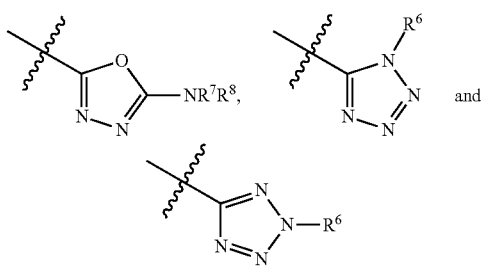

$R^2$ is selected from the group consisting of (a) —$C_{1-6}$alkyl optionally substituted with 1-3 of fluoro, (b) —$C_{3-6}$ cycloalkyl and

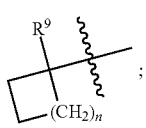

(c)

n is an integer selected from 0, 1, 2 and 3;
$R^3$ is selected from the group consisting of —H, —F, —OH, —$CH_3$ and —$CF_3$;
$R^4$ is selected from the group consisting of —H and —$C_{1-4}$ alkyl;
$R^5$ is selected from the group consisting of —H and —$CH_3$; and
$R^6$ is selected from the group consisting of —H, —$C_{1-6}$ alkyl optionally substituted with 1-3 fluoro, —$C_{3-6}$ cycloalkyl optionally substituted with 1-3 fluoro and —$CH_2$—$R^{10}$;
$R^7$ is selected from the group consisting of —H, —$C_{1-6}$ alkyl optionally substituted with 1-3 fluoro, —$C_{3-6}$ cycloalkyl optionally substituted with 1-3 fluoro, —$COC_{1-6}$ alkyl and —$COC_{3-6}$ cycloalkyl;
$R^8$ is selected from the group consisting of —H, —$C_{1-6}$ alkyl optionally substituted with 1-3 fluoro, and —$CH_{3-6}$ cycloalkyl optionally substituted with 1-3 fluoro;
$R^9$ is selected from the group consisting of —$CH_3$ and —F; and $R^{10}$ is selected from the group consisting of pyrrolidinyl optionally substituted on nitrogen with methyl, piperidinyl optionally substituted on nitrogen with methyl, and morpholinyl optionally substituted on nitrogen with methyl.

In another embodiment of this invention (referred to herein as "Embodiment A") are compounds of formula I wherein:

$R^1$ is selected from the group consisting of:

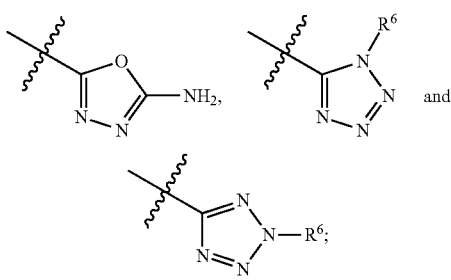

$R^2$ is selected from the group consisting of (a) —$C_{1-6}$alkyl optionally substituted with 1-3 fluoro, (b) —$C_{3-6}$ cycloalkyl and

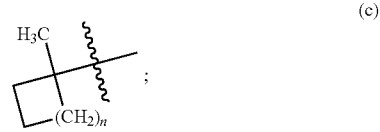

(c)

n is an integer selected from 0, 1, 2 and 3;
$R^3$ is selected from the group consisting of —H, —F, —OH, —$CH_3$ and —$CF_3$;
$R^4$ is selected from the group consisting of —H and —$C_{1-4}$ alkyl;
$R^5$ is selected from the group consisting of —H and —$CH_3$; and
$R^6$ is selected from the group consisting of —H and —$C_{1-3}$ alkyl.

The pyridyl-N-oxide analog within the scope of formula I can be structurally represented by:

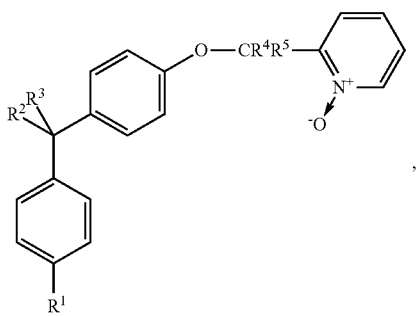

and includes the pharmaceutically acceptable salts, esters and solvates thereof.

In another embodiment of this invention are compounds of formula I having structural formula Ib

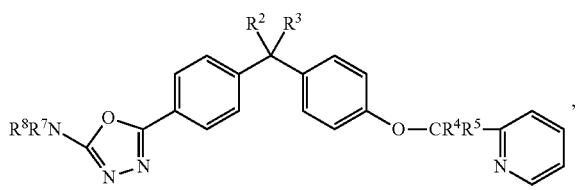

wherein the variables $R^2$, $R^3$, $R^4$, $R^5$, $R^7$ and $R^8$ are as defined in formula I, including the pyridyl-N-oxide analog of formula Ib, and the pharmaceutically acceptable salts, esters and solvates thereof. In a sub-embodiment are compounds of formula Ib wherein the variables $R^2$, $R^3$, $R^4$ and $R^5$ are as defined in Embodiment A and $R^7$ is —H and $R^8$ is —H.

In another embodiment are compounds of formula having structural formula Ic

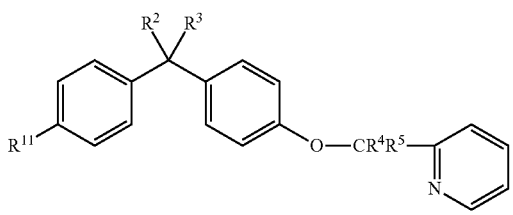

wherein $R^{11}$ is selected from

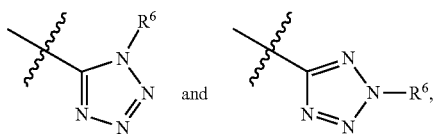

and the variables $R^2$, $R^3$, $R^4$, $R^5$ and $R^6$ are as defiled in formula I, including the pyridyl-N-oxide analog of formula Ic, and the pharmaceutically acceptable salts, esters and solvates thereof. In a sub-embodiment are compounds of formula Ic wherein the variables $R^2$, $R^3$, $R^4$, $R^5$ and $R^6$ are as defined in Embodiment A.

Within each of the embodiments and sub-embodiments defined by formulas I, Ib, Ic and Embodiment A is a first class of compounds wherein $R^2$ is —$C_{1-6}$alkyl optionally substituted with 1-3 fluoro. In a sub-class of each of the first classes of compounds are those wherein $R^2$ is selected from methyl, ethyl, propyl, i-propyl and —$C_4$alkyl, and in a further sub-class of each of the first classes $R^2$ is t-butyl.

Within each of the embodiments and sub-embodiments defined by formulas I, Ib, Ic and Embodiment A is a second class of compounds wherein $R^2$ is selected from —$C_{3-6}$ cycloalkyl and

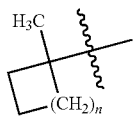

In a sub-class of each of the second classes of compounds are those wherein $R^2$ is selected from cyclopropyl, cyclobutyl, 1-methyl-cyclopropyl and 1-methyl cyclobutyl.

Within each of the embodiments and sub-embodiments defined by formulas I, Ib, Ic and Embodiment A, as well as within each of the first classes and sub-classes thereof and each of the second classes and sub-classes thereof defined above, is a third class of compounds wherein $R^3$ is selected from —H, —OH and methyl, and preferably $R^3$ is selected from —H and methyl.

Within each of the embodiments and sub-embodiments defined by formulas I, Ib, Ic and Embodiment A, as well as within each of the first classes and sub-classes thereof, and each of the second classes and sub-classes thereof, and each of the third classes, all defined above, is a fourth class of compounds wherein $R^4$ is selected from —H, methyl and ethyl, and more particularly $R^4$ is —H and $R^5$ is —H.

Within each of the embodiments defined by formulas I and Ib are compounds wherein $R^7$ is —H and $R^8$ is —H.

The invention is described herein in detail using the terms defined below unless otherwise specified. "Alkyl", means carbon chains which may be linear or branched, or combinations thereof, containing the indicated number of carbon atoms. Examples of alkyl groups include methyl, ethyl, propyl, isopropyl (i-propyl), butyl, sec- and tert-butyl (s-butyl, t-butyl), pentyl, hexyl, and the like. Cycloalkyl is intended to be a cyclized alkyl ring having the indicated number of carbon atoms Examples of cycloalkyl include cyclopropyl, cyclobutyl, cyclopentyl, and cyclohexyl.

Reference to the compounds of this invention as those of "formula I" "formula Ia," "formula Ib," "formula Ic" or any other generic structural formulas used herein is intended herein to encompass compounds falling within the scope of the structural formula including pyridyl-N-oxide analogs, and pharmaceutically acceptable, salts, esters and solvate forms thereof (including pharmaceutically acceptable, salts, esters and solvate forms of the pyridyl-N-oxide analogs) where such forms are possible, unless specified otherwise. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like, and particularly citric, fumaric, hydrobromic, hydrochloric, maleic, phosphoric, sulfuric, and tartaric acids.

Pharmaceutically acceptable esters of available hydroxy groups can optionally be formed as well. Examples of pharmaceutically acceptable esters include, but are not limited to, —$C_{1-4}$ alkyl and —$C_{1-4}$ alkyl substituted with phenyl-, dimethylamino- and acetylamino.

The compounds of formula I may contain one or more asymmetric centers, and can thus occur as racemates, racemic mixtures, single enantiomers, diastereoisomeric mixtures and individual diastereoisomers. The present invention includes all such isomers, as well as salts, esters and solvates of such racemates, mixtures, enantiomers and diastereoisomers. Furthermore, some of the crystalline forms of compounds of the present invention may exist as polymorphs and as such are intended to be included in the present invention. In addition, some of the compounds of the instant invention may form solvates with water or common organic solvents. Such solvates and hydrates are likewise encompassed within the scope of this invention.

Compounds of structural formula I may be separated into their individual diastereoisomers by, e.g., fractional crystallization from suitable solvents, e.g., DCM/hexanes or EtOAc/hexanes, or via chiral chromatography using an optically active stationary phase. Absolute stereochemistry may be determined by X-ray crystallography of crystalline products or crystalline intermediates which are derivatized, if necessary, with a reagent containing a stereogenic center of known configuration. Alternatively, any stereoisomer of a compound of the general formula I may be obtained by stereospecific synthesis using optically pure starting materials or reagents of known absolute configuration.

The ability of the compounds of this invention to inhibit biosynthesis of the leukotrienes makes them useful for preventing or reversing the symptoms induced by the leukotrienes in a human subject. Accordingly, this invention provides a method for preventing the synthesis, the action, or the release of leukotrienes in a mammal which comprises administering to said mammal a FLAP inhibitory effective amount of a compound of this invention. Such FLAP inhibitory activity can be measured using the FLAP Assay described herein. Since leukotrienes are potent inflammatory mediators, also provided is method of treating an inflammatory condition in a mammal which comprises administering a therapeutically effective amount of a compound of this invention to a mammal in need of such treatment.

The inhibition of the mammalian biosynthesis of leukotrienes also indicates that the compounds and pharmaceutical compositions thereof are useful to treat, prevent or ameliorate atherosclerosis in mammals, and especially in humans. Therefore, the compounds of formula I can be used for the treatment of atherosclerosis comprising administering a therapeutically effective amount of a compound of Formula I to a patient in need of such treatment. A further aspect of this invention involves a method for preventing or reducing the risk of developing atherosclerosis, comprising administering a prophylactically effective amount of a compound of formula I to a patient in need of such treatment, for example, a patient who is at risk of developing atherosclerosis.

Atherosclerosis is characterized by the deposition of atheromatous plaques containing cholesterol and lipids on the innermost layer of the walls of large and medium-sized arteries. Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction, are all clinical manifestations of atherosclerosis and are therefore encompassed by the terms "atherosclerosis" and "atherosclerotic disease."

A FLAP inhibitor may be administered to prevent or reduce the risk of occurrence, or recurrence where the potential exists, of a coronary heart disease (CHD) event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of a FLAP inhibitor to a patient at risk for such an event. The patient may already have atherosclerotic disease at the time of administration, or may be at risk for developing it.

The method of this invention particularly serves to prevent or slow new atherosclerotic lesion or plaque formation, and to prevent or slow progression of existing lesions or plaques, as well as to cause regression of existing lesions or plaques. Accordingly, one aspect of this invention encompassed within the scope of treatment of atherosclerosis involves a method for halting or slowing the progression of atherosclerosis, including halting or slowing atherosclerotic plaque progression, comprising administering a therapeutically effective amount of a FLAP inhibitor to a patient in need of such treatment. This method also includes halting or slowing progression of atherosclerotic plaques existing at the time the instant treatment is begun (i.e., "existing atherosclerotic plaques"), as well as halting or slowing formation of new atherosclerotic plaques in patients with atherosclerosis.

Another aspect of this invention encompassed within the scope of treatment of atherosclerosis involves a method for regression of atherosclerosis, including regression of atherosclerotic plaques existing at the time the instant treatment is begun, comprising administering a therapeutically effective amount of a FLAP inhibitor to a patient in need of such treatment. Another aspect of this invention involves a method for preventing or reducing the risk of atherosclerotic plaque rupture comprising administering a prophylactically effective amount of a FLAP inhibitor to a patient in need of such treatment.

The ability of the compounds of Formula I to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to prevent or reduce the risk for, treat or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such as angina, formation of atherosclerotic plaques, myocardial ischemia, hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, 16) multiple sclerosis, 17) proliferation of myoblastic leukemia cells, and 18) acne.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also act as inhibitors of tumor metastasis and exhibit cytoprotective action.

The FLAP inhibitors of this invention can also be administered for prevention, amelioration and treatment of glomerulonephritis (see Guasch A., Zayas C. F., Badr K F. (1999), "MK-591 acutely restores glomerular size selectivity and reduces proteinuria in human glomerulonephritis," Kidney Int., 56:261-267); and also for and prevention, amelioration and treatment of kidney damage resulting from diabetes complications (see Valdivielso J M, Montero A., Badr K F., Munger K A. (2003), "Inhibition of FLAP decreases proteinuria in diabetic rats," J. Nephrol., 16(1):85-940.)

In addition, the compounds of this invention can also be used for the treatment of chronic obstructive pulmonary disease (COPD). As described in S. Kilfeather, Chest, 2002, vol 121, 197, airway neutrophilia in COPD patients is believed to be a contributing source of inflammation and is associated with airway remodeling. The presence of neutrophils is mediated in part by $LTB_4$, and treatment with the instant compounds could be used to reduce neutrophilic inflammation in patients with COED.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like. Two assays can be used to measure cytoprotective ability. These assays are: (A) an ethanol-induced lesion assay and (B) an indomethacin-induced ulcer assay and are described in EP 140,684.

In particular, the compounds of the invention would be useful to reduce the gastric erosion caused by co-administration of a cyclooxygenase-2 selective inhibitor and low-dose aspirin. Cyclooxygenase-2 selective inhibitors are widely used as effective anti-inflammatory drugs with less potential for gastrointestinal complications as compared to traditional, non-selective non-steroidal anti-inflammatory drugs. However, the combined use of a cyclooxygenase-2 selective inhibitor with low-dose aspirin for cardio protection may compromise the gastrointestinal safety of this class of compounds. By virtue of its activity as a 5-lipoxygenase inhibitor, the compounds of the invention would be expected to be gastric protective in this regard. See Fiorucci, et at FASEB J. 17:1171-1173, 2003. Cyclooxygenase-2 selective inhibitors for use with the invention include but are not limited to etoricoxib (ARCOXIA™), celecoxib (CELEBREX®) and valdecoxib (BEXTRA™). A compound of this invention in combination with a cyclooxygenase-2 selective inhibitor could be administered in unit dosage form or separately to a patient on low-dose aspirin therapy. Alternatively, the cyclooxygenase-2 inhibitor could be administered in unit dosage form with low-dose aspirin, in which case a compound of this invention would be administered separately. All three active ingredients in unit dosage form is also encompassed. Conventional dosage amounts of the cyclooxygenase-2 selective inhibitor and aspirin (for cardio protection) may be utilized. Aspirin could be administered at 81 mg once daily.

In general, FLAP inhibitors can be identified as those compounds which have an $IC_{50}$ in the "FLAP Binding Assay" that is less than or equal to 1 µM, and preferably 500 nM or less.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of onset of atherosclerosis.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment to slow progression of existing atherosclerosis, and a prophylactically effective amount, e.g., for prevention of an atherosclerotic disease event or formation of new lesions.

An effective amount of a FLAP inhibitor in the method of this invention is in the range of about 0.01 mg/kg to about 30 mg/kg of body weight per day, preferably 0.1 mg to about 15 mg per kg, and most preferably 0.5 to 7.5 mg per kg, in single or divided doses. A single daily dose is preferred but not necessary. For an average body weight of 70 kg, the dosage level is therefore from about 1 mg to about 2000 mg of drug per day, e.g. 10 mg, 25 mg, 50 mg, 75 mg, 100 mg, 125 mg, 150 mg, 175 mg, 200 mg, 250 mg or 500 mg per day, preferably given as a single daily dose or in divided doses two to four times a day, or in sustained release form. It will be understood, however, that the specific dose level for any particular patient will depend upon a variety of factors including the age, body weight, general health, sex, diet, time of administration, route of administration, rate of excretion, drug combination and the severity of the patient's condition. A consideration of these factors is well within the purview of the ordinarily skilled clinician for the purpose of determining the therapeutically effective or prophylactically effective dosage amount needed to prevent, counter, or arrest the progress of the condition. It is expected that the FLAP inhibitor will administered chronically on a daily basis for a length of time appropriate to treat or prevent the medical condition relevant to the patient, including a course of therapy lasting months, years or the life of the patient.

One or more additional active agents may be administered with a compound of Formula I. The term "additional active agent (or agents)" is intended to mean a pharmaceutically active agent (or agents) different from the compound of formula I. In a broad embodiment, any suitable additional active agent or agents, including but not limited to anti-atherosclerotic agents such as a lipid modifying compound, anti-diabetic agents and/or anti-obesity agents, may be used in combination with the compound of formula I in a single dosage formulation, or may be administered to the patient in a separate dosage formulation, which allows for concurrent or sequential administration of the active agents. The additional active agent or agents can be lipid modifying compounds or agents having other pharmaceutical activities, or agents that have both lipid-modifying effects and other pharmaceutical activities. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin (see U.S. Pat. No. 4,342,767), simvastatin (see U.S. Pat. No. 4,444,784), pravastatin, particularly the sodium salt thereof (see U.S. Pat. No. 4,346,227), fluvastatin particularly the sodium salt thereof (see U.S. Pat. No. 5,354,772), atorvastatin, particularly the calcium salt thereof (see U.S. Pat. No. 5,273,995), pitavastatin also referred to as NK-104 (see PCT international publication number WO 97/23200) and rosuvastatin (CRESTOR®; see U.S. Pat. No. 5,260,440); 5-lipoxygenase inhibitors; cholesterol ester transfer protein (CETP) inhibitors, for example JTT-705 and torcetrapib, also known as CP529,414; HMO-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; niacin; niacin receptor agonists such as acipimox and acifran, as well as niacin receptor partial agonists; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABCA1 gene expression; PXR and LXR ligands including both inhibitors and agonists; bisphosphonate compounds such as alendronate sodium; and cyclooxygenase-2 inhibitors such as etoricoxib, celecoxib and valdecoxib.

Still another type of agent that can be used in combination with the compounds of this invention are cholesterol absorption inhibitors. Cholesterol absorption inhibitors block the movement of cholesterol from the intestinal lumen into enterocytes of the small intestinal wall. This blockade is their primary mode of action in reducing serum cholesterol levels. These compounds are distinct from compounds which reduce serum cholesterol levels primarily by mechanisms of action such as acyl coenzyme A-cholesterol acyl transferase (ACAT) inhibition, inhibition of triglyceride synthesis, MTP inhibition, bile acid sequestration, and transcription modulation such as agonists or antagonists of nuclear hormones. Cholesterol absorption inhibitors include but are not limited to those described in U.S. Pat. No. 5,846,966, U.S. Pat. No. 5,631,365, U.S. Pat. No. 5,767,115, U.S. Pat. No. 6,133,001, U.S. Pat. No. 5,886,171, U.S. Pat. No. 5,856,473, U.S. Pat. No. 5,756,470, U.S. Pat. No. 5,739,321, U.S. Pat. No. 5,919,672, U.S. Pat. No. 6,498,156, US2004/0082561, US2004/0067913, US2004/0063929, US2002-0137689, WO 05/047248, WO 05/021497, WO 05/021495, WO 05/000353, WO 04/005247, WO 00/63703, WO 00/60107, WO 00/38725, WO 00/34240, WO 00/20623, WO 97/45406, WO 97/16424, WO 97/16455, and WO 95/08532. An exemplary cholesterol absorption inhibitor is ezetimibe, marketed in the U.S. under the tradename ZETIA® described in U.S. Pat. No. Re 37721 and the Physician's Desk Reference.

This and other cholesterol absorption inhibitors can be identified according to the assay of hypolipidemic compounds using the hyperlipidemic hamster described in U.S. Pat. Re 37721, beginning in column 20, in which hamsters are fed a controlled cholesterol diet and dosed with test compounds for seven days. Plasma lipid analysis is conducted and data is reported as percent reduction of lipid versus control.

Therapeutically effective amounts of cholesterol absorption inhibitors include dosages of from about 0.01 mg/kg to about 30 mg/kg of body weight per day, preferably about 0.1 mg/kg to about 15 mg/kg. For an average body weight of 70 kg, the dosage level is therefore from about 0.7 mg to about 2100 mg of drug per day, e.g. 10, 20, 40, 100 or 200 mg per day, preferably given as a single daily dose or in divided doses two to six times a day, or in sustained release form. This dosage regimen may be adjusted to provide the optimal therapeutic response when the cholesterol absorption inhibitor is used in combination with a compound of the instant invention.

In the method of treatment of this invention, the FLAP inhibitors may be administered via any suitable route of administration such as orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred.

For oral use, the pharmaceutical compositions of this invention containing the active ingredient may be in forms such as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be far example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Oral immediate-release and time-controlled release dosage forms may be employed, as well as enterically coated oral dosage forms. Tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. One example of a time-controlled release device is described in U.S. Pat. No. 5,366,738. They may also be coated by the technique described in U.S. Pat. Nos. 4,256,108; 4,166,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier.

A therapeutically effective amount of a compound of Formula I can be used for the preparation of a medicament useful for treating or preventing any of the medical conditions described herein, in dosage amounts described herein. For example, a compound of Formula I can be used for the preparation of a medicament useful for preventing or reducing the risk of developing atherosclerotic disease, halting or slowing the progression of atherosclerotic disease once it has become clinically manifest, and preventing or reducing the risk of a first or subsequent occurrence of an atherosclerotic disease event. Additionally, the medicament may be useful for the treatment of asthma, allergies and allergic conditions, inflammation, COPD or erosive gastritis. The medicament comprised of a compound of Formula I may also be prepared with one or more additional active agents, such as those described herein.

The compounds of structural formula I of the present invention can be prepared according to the procedures of the following Schemes and Examples, using appropriate materials and are further exemplified by the specific examples which follow. Moreover, by utilizing the procedures described herein, one of ordinary skill in the art can readily prepare additional compounds of the present invention claimed herein. The compounds illustrated in the examples are not, however, to be construed as forming the only genus that is considered as the invention. All temperatures are degrees Celsius unless otherwise noted. Mass spectra (MS) were measured by electron-spray ion-mass spectroscopy (ES-MS).

The instant compounds are generally isolated in a pharmaceutically acceptable form which can either be the free base or an appropriate salt derivative, such as those described above. The free amine bases corresponding to the isolated salts can be generated by neutralization with a suitable base, such as aqueous sodium hydrogencarbonate, sodium carbonate, sodium hydroxide, or potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization.

Some abbreviations used herein are as follows:

Ar is Aryl; Bu is butyl; t-Bu is tert-butyl; celite is Celite® diatomaceous earth; DCM is dichloromethane; Dess-Martin Periodinane is 1,1,1-tris(acetyloxy)-1,1-dihydro-1,2-benzodoxol-3-(1H)-one; DIPEA is diisopropylethylamine; DMF is N,N-dimethylformamide; dppf is 1,1'-bis(diphenylphosphino)ferrocene; equiv. is equivalent(s); ES-MS is electron spray ion-mass spectroscopy; Et is ethyl; EtOAc is ethyl acetate; HATU is O-(7-azabenzotriazol-1-yl)-1,1,3,3-tetramethyluronium hexafluorophosphate; HetAr or HAR is Heteroaryl; HPLC is high performance liquid chromatography; i is Iso; LDA is lithium diisopropylamide; LG is leaving group; Me is methyl; m.p. is melting point; MS is mass spectrum, and a mass spectrum obtained by ES-MS may be denoted herein by "ES"; p is para; Ph is phenyl; Pr is propyl; i-Pr is isopropyl; p-TSA is para-toluenesulfonic acid; Tf is trifluoromethanesulfonyl; TFA is trifluoroacetic acid; and THF is tetrahydrofuran.

In the Schemes, all substituents are as defined above unless indicated otherwise.

Reaction scheme A illustrates the preferred method for synthesis of compounds of structural formula 3 and 4. In this method, a benzophenone of type 1 is treated with an organometallic reagent of type 2, capable of transferring an alkyl group, and the product of the reaction is a compound of structural formula 3. Preferred organometallic reagents for this transformation include organomagnesium (Grignard) or organolithium compounds. When Grignard reagents are employed as shown in scheme A, it is customary to conduct the reaction in a suitable ethereal solvent such as diethyl ether, or THF or mixtures thereof, at temperatures between −78° C. and the boiling temperature of the solvent. In the case of an organolithium reagent, the reaction can be conducted in a variety of solvents such as diethyl ether or hexanes, at temperatures between −78° C. and room temperature. The Grignard and the organolithium reagents are often purchased commercially, but can be prepared synthetically according to known methods in organic synthesis. Removal of the tertiary hydroxyl group in 3 will depend upon the identity of the $Z^1$ and $Z^2$ substituents. If these substituents are unaffected by hydrogenation conditions, then the hydroxyl group may be removed by hydrogenolysis using a palladium-on-carbon catalyst in a solvent such as methanol or ethanol and in the presence of hydrogen gas or a hydrogen donor such as formic acid. Occasionally it may be the case that either one or both of the $Z^1$ and $Z^2$ substituents are sensitive to hydrogenation conditions, and in these instances 3 is reacted with a organosilane such as triethylsilane in the presence of a protic acid like TFA or a Lewis acid like boron trifluoride. It is customary to conduct the reaction in an inert organic solvent like DCM or 1,2-dichloroethane at temperatures between 0° C. and boiling point of the solvent. Depending on the nature of the $Z^1$ and $Z^2$ substituents, compound 4 can then be transformed to other compounds of the present invention.

Scheme A

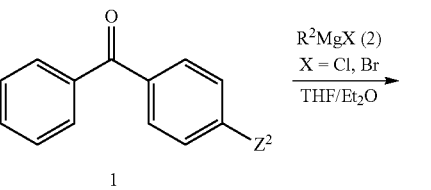

1

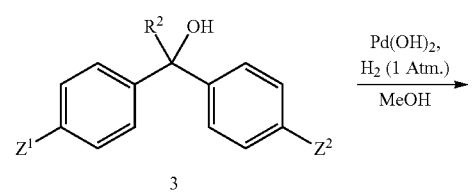

3

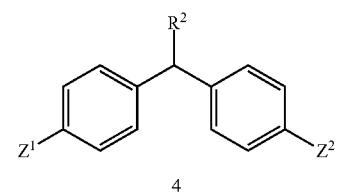

4

$Z^1 = R^1$ as defined in formula I or a group that can be converted to $R^1$
$Z^2 = $ ─O─$CR^4R^5$─ pyridyl as shown in formula I or a group that can be converted to it Reaction scheme B illustrates an alternative method for the synthesis of diarylalcohols of type 3. In this method, an alkyl-aryl ketone of type 5 is treated with an organometallic reagent of type 6, capable of transferring an aryl group. Preferred organometallic reagents for effecting this transformation include organomagnesium (Grignard) or organolithium con pounds, and are used in a similar manner to that described above. In yet another variation of this method, 3 can also be prepared from the reaction of an alkyl-aryl ketone of type 7 and a organometallic reagent of type 8.

Scheme B

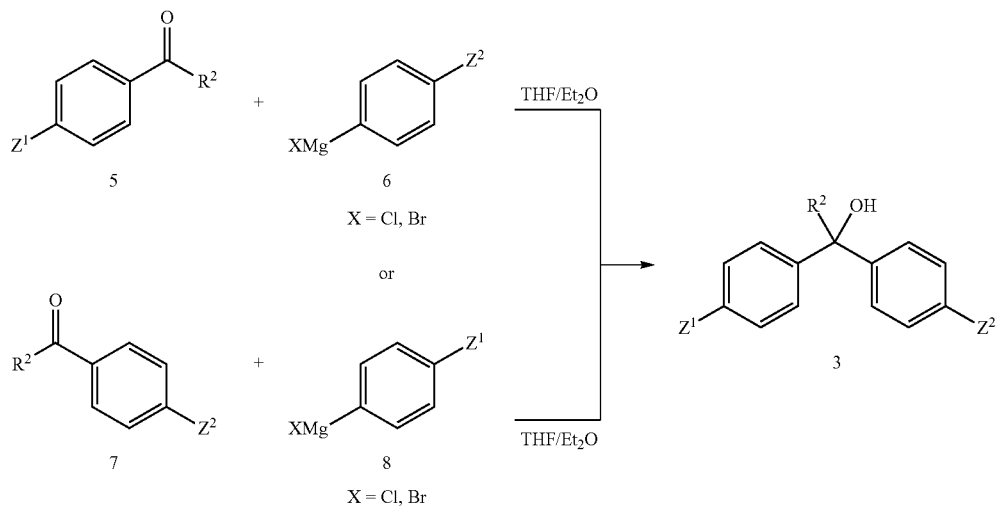

Reaction scheme C illustrates a general method for the synthesis of compounds of type 13 ($Z^1$, $Z^2$=OH). In this method, an aldehyde of type 9 can be arylated twice in an electrophilic aromatic substitution process called the Friedel-Crafts reaction. Typical conditions for affecting such an arylation include initial addition of one aromatic-coupling partner of type 10 to the aldehyde 9 to afford an intermediary alcohol of type 11, subsequent generation of an intermediate secondary carbocation of type 12, derived from 11, followed by in situ trapping with a second aromatic-coupling partner of type 10 which may or may not be the same as the first aromatic coupling partner. Formation of 12 may occur spontaneously in solution or it may be promoted with a reagent capable of ionizing 11, like a protic acid such as p-TSA, or concentrated hydrochloric acid or a suitable Lewis acid. In certain cases, it may be preferable to conduct the reaction in the presence of a free radical scavenger such as 3-mercaptopropionic acid or the like. The reaction is conducted typically in an inert organic solvent, at temperatures between −20° C. and the boiling temperature of the solvent. The product is a compound of type 13, which can be elaborated to compounds of the present invention as described in the subsequent schemes.

Scheme C

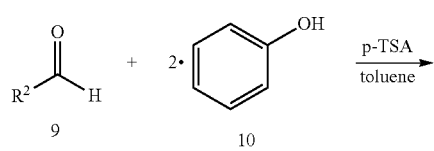

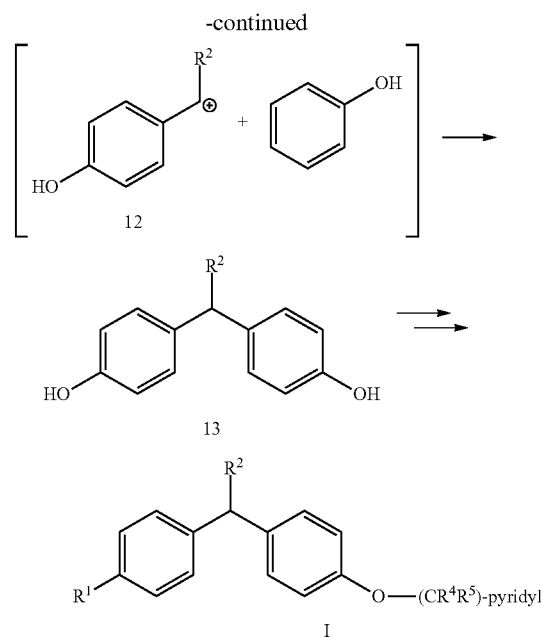

Reaction scheme D illustrates the preferred method for the preparation of compounds of type 15 ($Z^1$, $Z^2$=OH). In this method, a ketone of type 14 can be arylated twice using the Friedel-Crafts arylation methodology described above. The product is a compound of type 15 which can be elaborated to compounds of the present invention as described in the subsequent schemes.

Scheme D

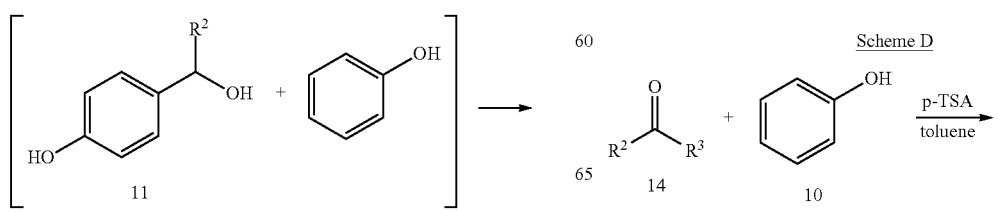

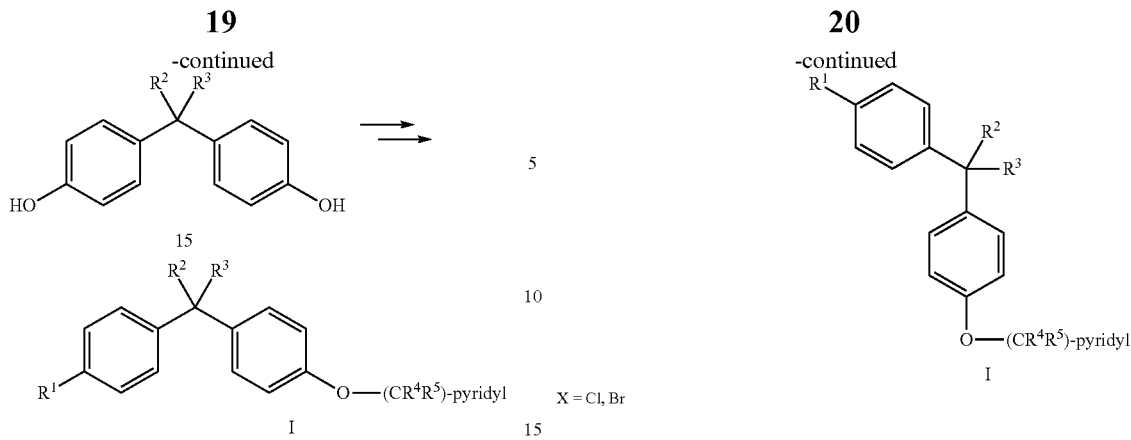

Reaction scheme E illustrates the preferred method for the generation of compounds of type 17 ($Z^1 \neq OH$). In this method, each of the aromatic coupling partners are introduced sequentially, but in separate chemical manipulations. For example, in scheme E, the aromatic coupling partners are introduced using a combination of the aforementioned Grignard and Friedel-Crafts acylation methodologies. Conditions for affecting the latter transformations are as described above.

Scheme F illustrates that compounds of structural formula 18 can be elaborated to the $R^1$ heterocyclic derivatives of structural formula 19 using known methods in organic synthesis. Specific examples of such transformations are shown in the Examples section.

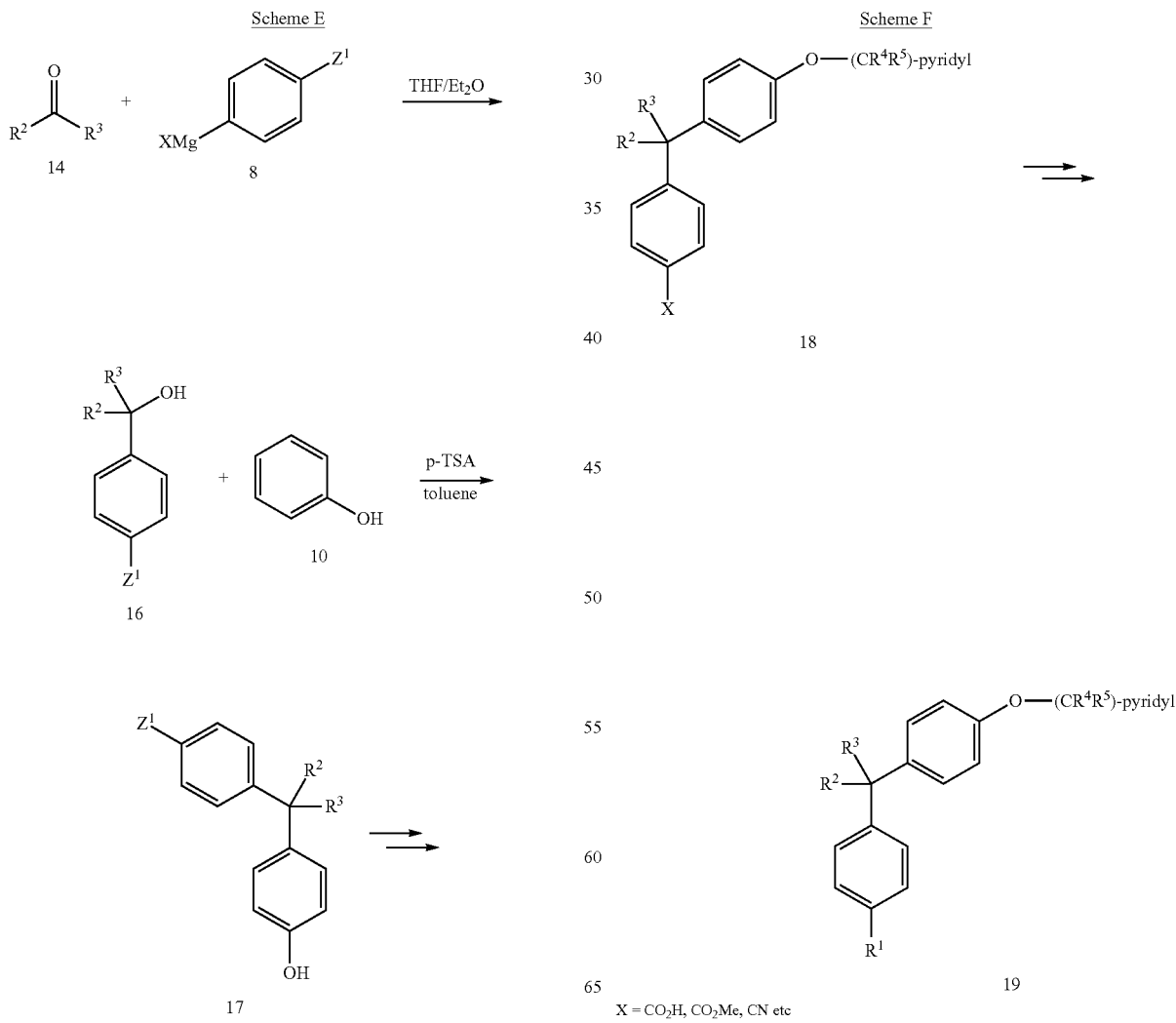

Scheme G illustrates the preferred method for the resolution of a compound of structural formula 20 in which the asterisked carbon is a center of chirality. Generally, the latter, or intermediates en route to their preparation, may be resolved to afford enantiomerically pure compounds such as 21 and 22 by chiral stationary phase liquid chromatography techniques or other suitable methods known in organic synthesis.

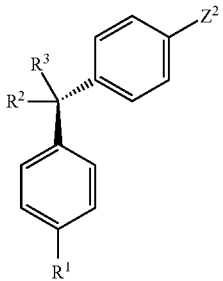

22

The following examples are provided to illustrate the invention and are not to be construed as limiting the scope of the invention in any manner.

The following structural formula Ia may be used in the following schemes and examples:

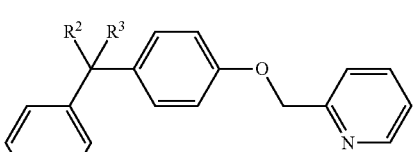

Ia

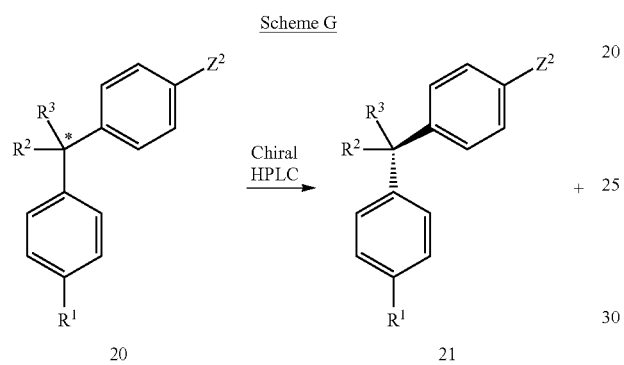

Preparation of Intermediates:

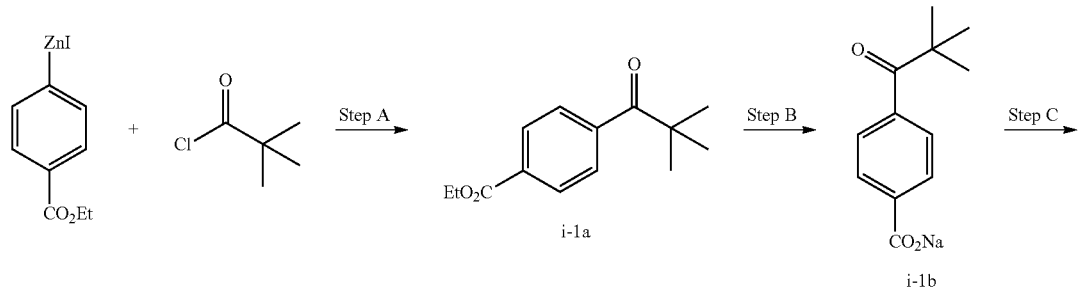

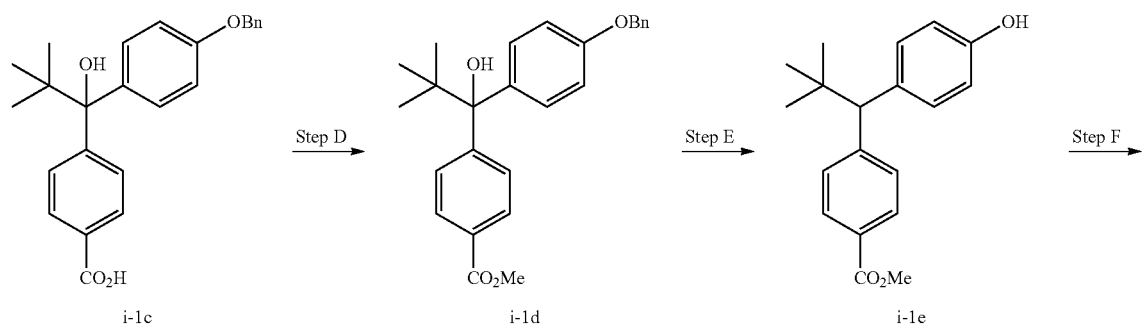

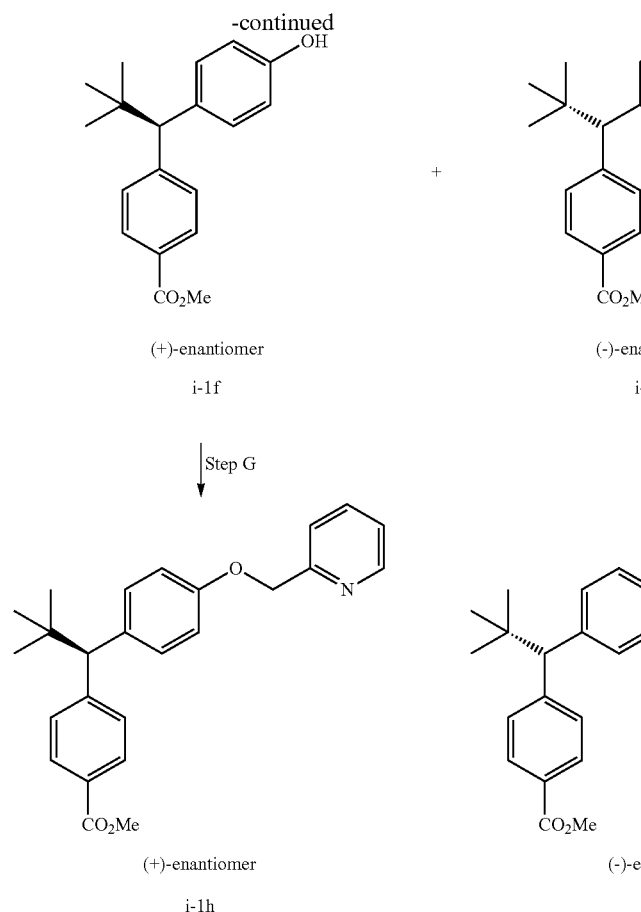

Preparation of i-1h and i-1i

Step A: Preparation of ethyl 4-(2,2-dimethylpropanoyl)benzoate (i-1a)

4-(Ethoxycarbonyl)phenyl-zinc iodide (50.0 mL of a 0.5 M solution in THF, 25.0 mmol) was added slowly via cannula to a stirred solution of dichlorobis(triphenylphosphine)palladium(II) (484 mg, 0.690 mmol) in THF (50 mL) at 0° C. After 15 min, trimethylacetyl chloride (2.80 mL, 22.7 mmol) was added and the resulting mixture was stirred at 0° C. for 1.5 h. The reaction mixture was poured into 1 N HCl and extracted three times with EtOAc. The combined organic extracts were washed with water, brine, dried ($MgSO_4$) and concentrated in vacuo. Purification of the crude residue by flash chromatography on silica gel (gradient elution; 0-10% EtOAc/hexanes as eluent) afforded the title compound i-1a. $^1$HNMR (500 MHz, $CDCl_3$): δ 8.08 (d, 2H, J=8.5 Hz), 7.67 (d, 2H, J=8.5 Hz), 4.42 (q, 2H, J=7.2 Hz), 1.42 (t, 3H, J=7.2 Hz), 1.36 (s, 9H).

Step B: Preparation of sodium 4-(2,2-dimethylpropanoyl)benzoate (i-1b)

Lithium hydroxide monohydrate (1.50 g, 35.7 mmol) was added to a stirred solution of i-1a (3.20 g, 13.7 mmol) in dioxane/water (20 mL:8.0 mL, respectively) and the resulting mixture was heated to 50° C. for 1 h. After cooling to room temperature, the reaction mixture was poured into 0.5 N HCl and extracted three times with EtOAc. The combined organic extracts were washed with water, brine, dried ($MgSO_4$) and concentrated in vacuo. The crude residue was suspended in methanol, and sodium methoxide (4.0 mL of 25% wt solution in methanol) was added. After 30 min, the volatiles were evaporated in vacuo to afford the title compound i-1b, which was used without further purification in the subsequent step.

Step C: Preparation of 4-{1-[4-(benzyloxy)phenyl]-1-hydroxy-2,2-dimethylpropyl}benzoic acid (i-1c)

Lithium chloride (2.00 g, 47.2 mmol) was added to an appropriately sized round bottom flask and then fused under vacuum using a gentle flame source. Magnesium turnings (730 mg, 30.4 mmol), iodine (a few crystals), 1-(benzyloxy)-4-bromobenzene (7.90 g, 30.0 mmol) and THF (30 mL) were added and the resulting mixture was heated at 50° C. until the magnesium metal was consumed. After cooling to room temperature the resulting solution was added slowly via syringe pump to a stirred solution of i-1b (3.30 g, 14.5 mmol) in THF (100 mL) at 0° C. After approximately 3 h, the reaction mixture was poured into 1 N HCl and extracted three times with EtOAc. The combined organic extracts were washed with water, brine, dried ($MgSO_4$) and concentrated in vacuo to give the title compound i-1c, which was used without further purification in the subsequent step. $^1$HNMR (500 MHz, $CDCl_3$): δ 8.04 (d, 2H, J=8.6 Hz), 7.63 (d, 2H, J=8.6 Hz), 7.50 (d, 2H, J=9.0 Hz), 7.52-7.36 (m, 5H), 6.93 (d, 2H, J=9.0 Hz) 5.08 (s, 2H), 1.22 (s, 9H).

Step D: Preparation of methyl 4-{1-[4-(benzyloxy)phenyl]-1-hydroxy-2,2-dimethylpropyl}benzoate (i-1d)

Cesium carbonate (5.70 g, 17.5 mmol) and iodomethane (2.70 mL, 43.4 mmol) were added to a solution of i-1c (5.70 g, 14.6 mmol) in DMF (70 mL). After approximately 2 h, the reaction was quenched by the addition of saturated aqueous ammonium chloride. The resulting mixture was poured into water and extracted three times with EtOAc. The combined organic extracts were washed with water, brine, dried (MgSO$_4$) and concentrated in vacuo. Purification of the crude residue by flash chromatography on silica gel (gradient elution; 0-10% EtOAc/hexanes as eluent) afforded the title compound i-1d. $^1$HNMR (500 MHz, CDCl$_3$): δ 7.94 (d, 2H, J=8.6 Hz), 7.58 (d, 2H, J=8.6 Hz), 7.47 (d, 2H, J=9.0 Hz), 7.47-7.34 (m, 5H), 6.90 (d, 2H, J=9.0 Hz), 5.05 (s, 2H), 3.92 (s, 3H), 1.18 (s, 9H).

Step E: Preparation of methyl 4-[1-(4-hydroxyphenyl)-2,2-dimethylpropyl]benzoate (i-1e)

A mixture of i-1d (2.60 g, 6.70 mmol) and palladium hydroxide (800 mg of 20 wt. % on activated carbon) in ethanol (60 mL) was hydrogenated at atmospheric pressure for approximately 72 h. The resulting mixture was filtered through a short column of Celite®, eluting copiously with DCM. The filtrate was concentrated in vacuo and the crude residue was purified by flash chromatography on silica gel (gradient elution; 5-20% EtOAc/hexanes as eluent) to afford the title compound i-1e. $^1$HNMR (500 MHz, CDCl$_3$): δ 7.96 (d, 2H, J=8.4 Hz), 7.49 (d, 2H, J=8.4 Hz), 7.30 (d, 2H, J=8.5 Hz), 6.78 (d, 2H, J=8.5 Hz), 3.92 (s, 3H), 3.75 (s, 1H), 1.03 (s, 9H).

Step F: Preparation of (i-1 f) and (i-1g)

Enantiomers i-1f and i-1g were separated using preparative supercritical fluid chromatography. A solution of i-1e (1.8 g) in methanol (9 mL) was injected (9×1 mL) onto a Chiralpak® AD (available from Chiral Technologies, Inc., Exton, Pa.) semi-preparative (250×20 mm) HPLC column (eluting with 40% methanol/CO$_2$ at 50 mL/min, 100 bar outlet pressure with UV detection at 220 nm). The enantiomers were separated with the faster eluting enantiomer i-1f having a retention time of ~3.25 min and the slower eluting enantiomer i-1 having a retention time of ~4.90 min. The eluants were concentrated to provide the enantiomers i-1f (α$_D$+9.21° (c=0.01, chloroform)) and i-1g (α$_D$-10.2° (c=0.01, chloroform)).

Step G: Preparation of methyl 4-{2,2-dimethyl-1-[4-(pyridin-2-ylmethoxy)phenyl]propyl}-benzoate (i-1i) (Formula Ia wherein R$^1$ is —CO$_2$Me, R$^2$ is -t-butyl, R$^3$ is —H)

Cesium carbonate (2.10 g, 6.45 mmol), potassium iodide (490 mg, 2.95 mmol), and 2-picolyl chloride hydrochloride (460 mg, 2.80 mmol) were added to a stirred solution of i-1g (800 mg, 2.68 mmol) in DMF (25 mL). After approximately 18 h, the reaction mixture was quenched by the addition of saturated aqueous ammonium chloride. The resulting mixture was poured into water and extracted three times with EtOAc. The combined organic extracts were washed with saturated aqueous sodium bicarbonate, water, brine, dried (MgSO$_4$) and concentrated in vacuo to afford the title compound i-1i (α$_D$-4.80°c=0.01, chloroform). $^1$HNMR (500 MHz, CDCl$_3$): δ 8.59 (d, 1H, J=4.3 Hz), 7.94 (d, 2H, J=8.3 Hz), 7.72 (dt, 1H, J=1.8, 7.8 Hz), 7.52 (d, 1H, J=8.0 Hz), 7.49 (d, 2H, J=8.3 Hz), 7.34 (d, 2H, J=8.8 Hz), 7.23 (dd, 1H, J=5.1, 7.4 Hz), 6.92 (d, 2H, J=8.8 Hz), 5.19 (s, 2H) 3.90 (s, 3H), 3.75 (s, 1H), 1.02 (s, 9H). In a similar manner, Intermediate i-1f was converted to i-1 h (α$_D$+7.70°, c=0.01, chloroform).

Scheme i-2

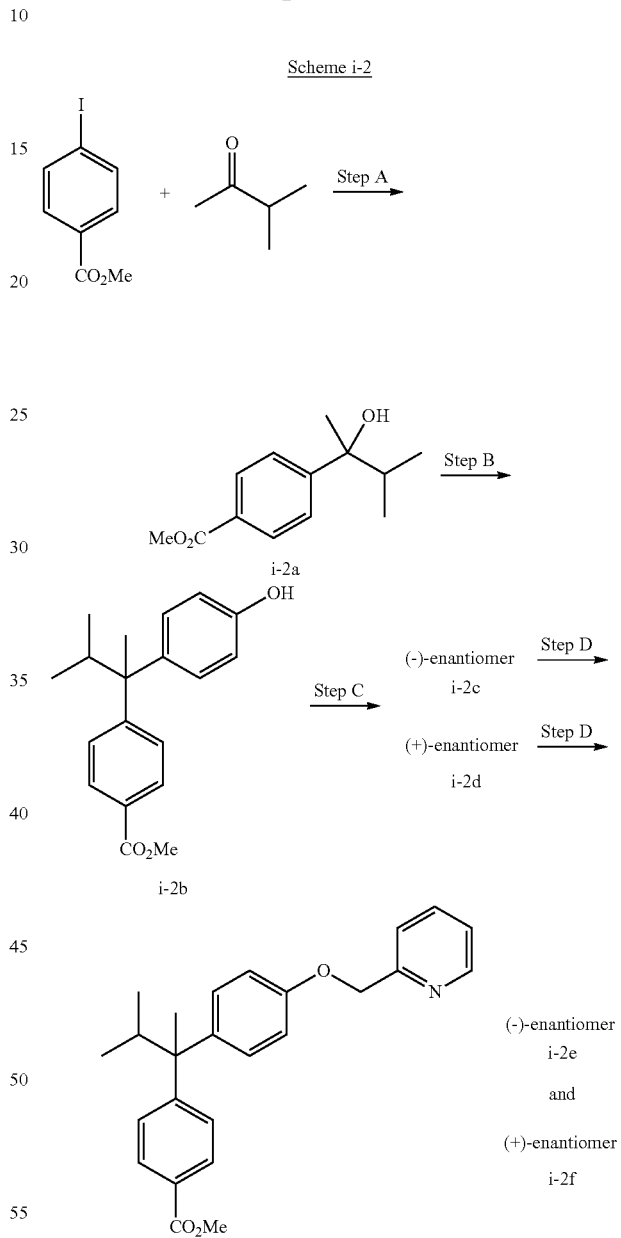

Preparation of i-2e and i-2f

Step A: Preparation of methyl 4-(1-hydroxy-1,2-dimethylpropyl)benzoate (i-2a)

Isopropyl magnesium chloride (12.0 mL of a 2 M solution in THF, 24.0 mmol) was added to a solution of methyl 4-iodobenzoate (5.24 g, 20.0 mmol) in THF (50 mL) at −40° C.

After 1 h, a second portion of isopropyl magnesium chloride (5.00 ml, of a 2 M solution in THF, 10.0 mmol) was added and the resulting mixture allowed to stir at −40° C. for 4 h. 3-Methyl-2-butanone (2.10 mL, 19.6 mmol) was then added and the resulting mixture allowed to warm to room temperature overnight. The reaction mixture was poured into 1 N HCl and extracted three times with EtOAc. The combined organic extracts were washed water, brine, dried (MgSO$_4$) and concentrated in vacuo. Purification of the crude residue by flash chromatography on silica gel (gradient elution; 0%-20% EtOAc/hexanes as eluent) afforded the title compound i-2a. $^1$HNMR (500 MHz, CDCl$_3$): δ 8.02 (d, 2H, J=8.5 Hz), 7.52 (d, 2H, J=8.5 Hz), 3.95 (s, 3H), 2.05 (p, 1H, J=6.6 Hz), 1.57 (s, 3H), 0.95 (d, 3H, J=6.6 Hz), 0.80 (d, 3H, J=6.9 Hz).

Step B: Preparation of methyl 4-[1-(4-hydroxyphenyl)-1,2-dimethylpropyl]benzoate (i-2b)

p-TSA (600 mg, 3.15 mmol), phenol (900 mg, 9.54 mmol) and i-2a (1.41 g, 6.35 mmol) were added to a preheated round-bottom flask at 95° C., and the resulting mixture was then heated to 120° C. for 2.0 h. After cooling to room temperature, the crude residue was purified by flash chromatography on silica gel (gradient elution; 0%-10% EtOAc/hexanes as eluent) to afford the title compound i-2b. $^1$HNMR (500 MHz, CDCl$_3$): δ 7.93 (d, 2H, J=8.5 Hz), 7.33 (d, 2H, J=8.5 Hz), 7.10 (d, 2H, J=8.7 Hz), 6.74 (d, 2H, J=8.7 Hz), 3.91 (s, 3H), 2.70 (s, 1H J=6.7 Hz), 1.61 (s, 3H), 0.87 (d, 3H, J=6.7 Hz), 0.83 (d, 3H, J=6.7 Hz).

Step C: Preparation of (i-2c) and (i-2d)

Enantiomers i-2c and i-2d were separated using preparative normal phase chiral HPLC. A solution of i-2b (360 mg) in isopropanol (4.5 mL of a 1:4 mixture) was injected (9×0.5 mL) onto a Chiralpak® AD (available from Chiral Technologies, Inc., Exton, Pa.) semi-preparative (250×20 mm) HPLC column (eluting with 30% isopropanol/heptanes at 9 ml/min with UV detection at 254 nm). The enantiomers were separated with the faster eluting enantiomer i-2c having a retention time of 18.9 min and the slower eluting enantiomer i-2d having a retention time of 21.6 min. The eluants were concentrated to provide the enantiomers i-2c and i-2d.

Step D: Preparation of methyl 4-{1,2-dimethyl-1-[4-(pyridin-2-ylmethoxy)phenyl]propyl}-benzoate (i-2e) (Formula Ia wherein R$^1$ is —CO$_2$Me, R$^2$ is -isopropyl, R$^3$ is -Me)

Intermediate i-2e was prepared from i-2c following the above procedure as described for i-1i. m/z (ES) 390 (MH)$^+$. $^1$HNMR (500 MHz, CDCl$_3$): δ 8.61 (d, 1H, J=4.6 Hz), 7.93 (d, 2H, J=8.7 Hz), 7.74 (t, 1H, J=7.7 Hz), 7.55 (d, 1H, J=7.8 Hz), 7.33 (d, 2H, J=8.7 Hz), 7.23 (m, 1H), 7.16 (d, 2H, J=0.8.7 Hz), 6.90 (d, 2H, J=8.7 Hz), 5.20 (s, 2H), 3.90 (s, 3H), 2.71 (s, 1H, J=6.6 Hz), 1.62 (s, 3H), 0.87 (d, 3H, J=6.6 Hz), 0.83 (d, 3H, J=6.6 Hz).

In a similar manner, Intermediate i-2d was converted to i-2f.

Preparation of i-3d

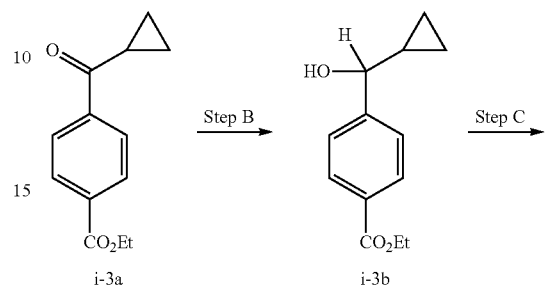

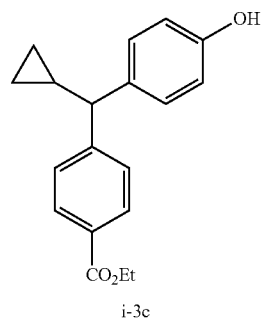

Step A: Preparation of ethyl 4-(cyclopropylcarbonyl)benzoate (i-3a)

Intermediate i-3a was prepared from 4-ethoxycarbonylphenyl zinc iodide and cyclopropanecarbonyl chloride following the above procedure as described for intermediate i-1a. m/z (ES) 219 (MH)$^+$. $^1$HNMR (500 MHz, CDCl$_3$): δ 8.17 (d, 2H, J=8.5 Hz), 8.08 (d, 2H, J=8.4 Hz), 4.44 (q, 2H, J=7.1 Hz), 2.71 (m, 1H), 1.45 (t, 3H, J=7.1 Hz), 1.31 (m, 2H), 1.13 (m, 2H).

Step B: Preparation of ethyl 4-[cyclopropyl(hydroxyl)methyl]benzoate (i-3b)

Sodium borohydride (107 mg, 2.82 mmol) was added in several portions to a stirred solution of i-3a (1.23 g, 5.64 mmol) in ethanol (30 mL) at room temperature. After 2 h, an additional portion of sodium borohydride (75.0 mg, 1.98 mmol) was added. After 1 h, the volatiles were removed in vacuo, and the crude residue partitioned between EtOAc and 0.5 N HCl. The organic phase was separated, washed with brine, dried (Na$_2$SO$_4$) and concentrated in vacuo. Purification of the crude residue by flash chromatography on silica gel (gradient elution; 10%-25% EtOAc/hexanes as eluent) afforded the title compound i-3b. $^1$HNMR (500 MHz, CDCl$_3$): δ 8.06 (d, 2H, J=8.2 Hz), 7.53 (d, 2H, J=8.3 Hz), 4.41

(q, 2H, J=7.1 Hz), 4.11 (d, 1H, J=8.2 Hz), 1.42 (t, 3H, J=7.1 Hz), 1.23 (m, 1H), 0.68 (m, 1H), 0.62 (m, 1H), 0.51 (m, 1H), 0.46 (m, 1H).

Step C: Preparation of ethyl 4-[cyclopropyl(4-hydroxyphenyl)methyl]benzoate (i-3c)

Intermediate i-3c was prepared from i-3b following the above procedure as described for intermediate i-2b. m/z (ES) 297 (MH)+.

Step D: Preparation of ethyl 4-{cyclopropyl[4-(pyridin-2-ylmethoxy)phenyl]methyl}benzoate (i-3d) (Formula Ia wherein $R^1$ is —$CO_2Et$, $R^2$ is -cyclopropyl, $R^3$ is —H)

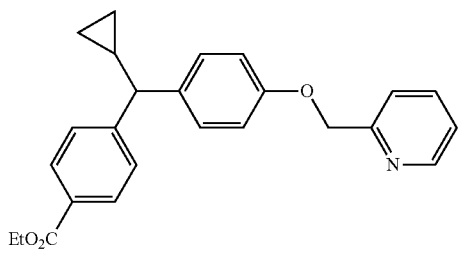

i-3d

Intermediate i-3d was prepared from i-3c following the above procedure as described for intermediate i-1i. m/z (ES) 388 (MH)+. $^1$HNMR (500 MHz, CDCl$_3$): δ 8.62 (d, 1H, J=4.8 Hz), 7.99 (d, 2H, J=8.3 Hz), 7.74 (dt, 1H, J=1.8, 7.8 Hz), 7.56 (d, 1H, J=7.7 Hz), 7.34 (d, 2H, J=8.2 Hz), 7.25 (dd, 1H, J=5.4, 7.0 Hz), 7.19 (d, 2H, J=8.7 Hz), 6.95 (d, 2H, J=8.7 Hz), 5.21 (s, 2H), 4.39 (q, 2H, J=7.1 Hz), 3.24 (d, 1H, J=9.4 Hz), 1.40 (t, 3H, J=7.1 Hz), 1.39 (m, 1H), 0.69 (m, 2H), 0.31 (m, 2H).

Preparation of ethyl 4-{2-methyl-1-[4-(pyridin-2-ylmethoxy)phenyl]propyl}benzoate (i-3e) (Formula Ia wherein $R^1$ is —$CO_2Et$, $R^2$ is -isopropyl, $R^3$ is —H)

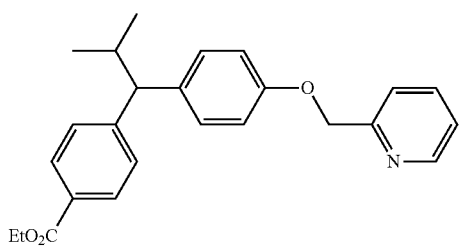

i-3e

Intermediate i-3e was prepared using isobutyryl chloride in place of cyclopropanecarbonyl chloride following the procedures as described for making i-3d. m/z (ES) 390 (MH)+. $^1$HNMR (500 MHz, CDCl$_3$): δ 8.60 (d, 1H, J=5.2 Hz), 7.96 (d, 2H, J=8.5 Hz), 7.72 (dt, 1H, J=1.6, 7.6 Hz), 7.53 (d, 1H, J=7.7 Hz), 7.35 (d, 2H, J=8.3 Hz), 7.24 (m, 1H), 7.20 (d, 2H, J=8.7 Hz), 6.92 (d, 2H, J=8.7 Hz), 5.18 (s, 2H), 4.37 (q, 2H, J=7.1 Hz), 3.45 (d, 1H, J=10.7 Hz), 2.48 (m, 1H), 1.29 (t, 3H, J=7.1 Hz), 0.91 (d, 3H, J=6.7 Hz), 0.88 (d, 3H, J=6.4 Hz).

Compounds wherein $R^2$ is —$C_{1-6}$alkyl substituted with 1-3 of fluoro, for example compounds 1aa and 1bb in Table 1 below, can be prepared by standard fluorination procedures on the appropriate intermediate (for example, fluorination of an intermediate similar to i-3a wherein the cyclopropyl group is replaced by isopropyl). For example, fluorination can be accomplished by base catalyzed enolization followed by trapping with an electrophilic fluorinating agent such as chlorodifluoromethane or iodotrifluoromethane.

Preparation of i-4d

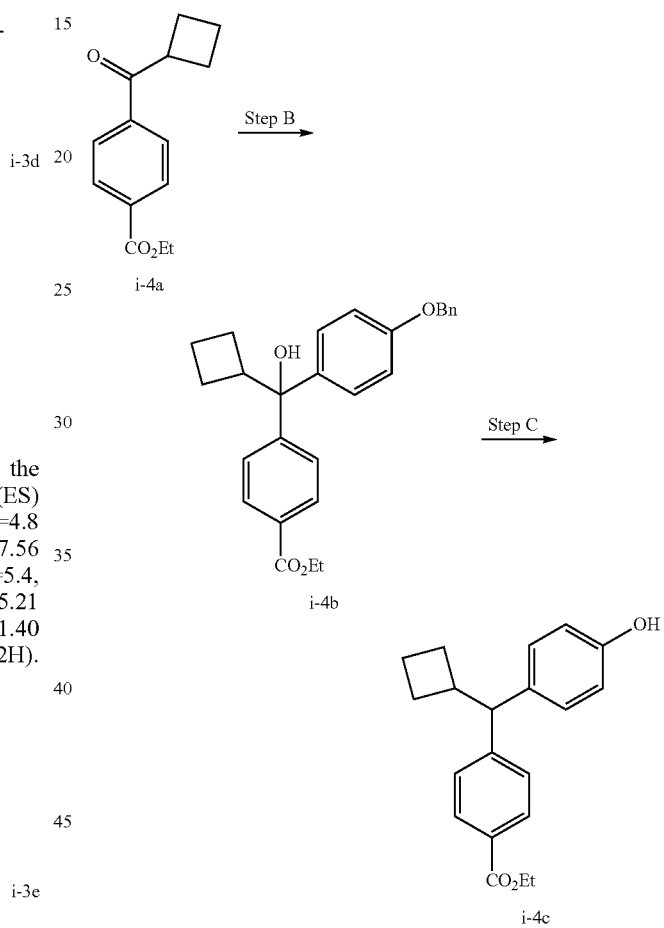

Step A: Preparation of ethyl 4-(cyclobutylcarbonyl)benzoate (i-4-a)

Intermediate i-4a was prepared from 4-ethoxycarbonylphenyl zinc iodide and cyclobutanecarbonyl chloride following the above procedure as described for intermediate i-1a. $^1$HNMR (500 MHz, CDCl$_3$): δ 8.13 (d, 2H, J=8.2 Hz), 7.96 (d, 2H, J=8.3 Hz), 4.43 (q, 2H, J=7.1 Hz), 4.04 (dt, 1H, J=6.9, 7.4 Hz), 2.44 (m, 2H), 2.34 (m, 2H), 2.14 (m, 1H), 1.96 (m, 1H), 1.43 (t, 3H, J=7.0 Hz).

Step B: Preparation of ethyl 4-{[4-(benzyloxy)phenyl](cyclobutyl)hydroxymethyl}benzoate (i-4-b)

A stirred mixture of magnesium turnings (80.0 mg, 3.33 mmol), iodine (a few crystals) and 1-(benzyloxy)-4-bromobenzene (873 mg, 3.32 mmol) in THF (10 mL) was heated at reflux until the magnesium metal was consumed. The resulting mixture was cooled to room temperature and added dropwise to a stirred solution of i-4-a (774 mg, 3.33 mmol) in THF (5.0 mL) at 0° C. After approximately 5 h, the reaction mixture was poured into 0.5 N HCl and extracted twice with EtOAc. The combined organic extracts were washed with brine, dried (Na$_2$SO$_4$) and concentrated in maw. Purification of the crude residue by flash chromatography on silica gel (isocratic elution; 10% EtOAc/hexanes as eluent) afforded the title compound i-4-b. m/z (ES) 399 (M-OH)$^+$. $^1$HNMR (500 MHz, CDCl$_3$): δ 7.96 (d, 2H, J=8.4 Hz), 7.45 (m, 7H), 7.28 (d, 2H, J=8.7 Hz), 6.91 (d, 2H, J=8.9 Hz), 5.05 (s, 2H), 4.37 (q, 2H, J=7.1 Hz), 3.39 (dt, 1H, J=7.2, 8.3 Hz), 2.10 (m, 3H), 1.87 (m, 1H), 1.72 (m, 2H), 1.39 (t, 3H, J=7.0 Hz).

Step C: Preparation of ethyl 4-[cyclobutyl(4-hydroxyphenyl)methyl]benzoate (i-4c)

A mixture of i-4b (386 mg, 0.927 mmol) and palladium hydroxide (50.0 mg of 20 wt. % on activated carbon) in methanol (10 mL) was hydrogenated at atmospheric pressure for 9 h. The resulting mixture was filtered through a short column of Celite, eluting copiously with ethyl acetate. The filtrate was concentrated in vacuo and the crude residue purified by flash chromatography on silica gel (gradient elution; 10%-15% EtOAc/hexanes as eluent) to afford the title compound i-4c. $^1$HNMR (500 MHz, CDCl$_3$): δ 7.96 (d, 2H, J=8.3 Hz), 7.26 (d, 2H, J=8.2 Hz), 7.06 (d, 2H, J=8.7 Hz), 6.76 (d, 2H, J=8.4 Hz), 4.37 (q, 2H, J=7.1 Hz), 3.88 (d, 1H, J=11 Hz), 3.03 (dt, 1H, J=8.1, 11 Hz), 2.05 (m, 2H), 1.90 (m, 2H), 1.75 (m, 2H), 1.39 (t, 3H, J=7.1 Hz).

Step D: Preparation of ethyl 4-{cyclobutyl[4-(pyridin-2-ylmethoxy)phenyl]methyl}benzoate (i-4-d) (Formula Ia wherein R$^1$ is —CO$_2$Et, R$^2$ is -cyclobutyl, R$^3$ is —H)

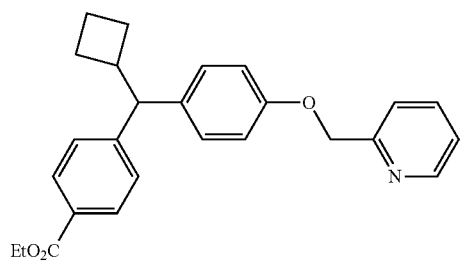

i-4d

Intermediate i-4-d was prepared from i-4c following the above procedure as described for intermediate i-1i. m/z (ES) 402 (MH)$^+$. $^1$HNMR (500 MHz, CDCl$_3$): δ 8.61 (d, 1H, J=4.8 Hz), 7.95 (d, 2H, J=8.2 Hz), 7.73 (dt, 1H, J=1.7, 7.7 Hz), 7.54 (d, 1H, J=8.0 Hz), 7.26 (d, 2H, J=8.3 Hz), 7.24 (m, 1H), 7.11 (d, 2H, J=8.6 Hz), 6.92 (d, 2H, J=8.7 Hz), 5.19 (s, 2H), 4.37 (q, 2H, J=7.1 Hz), 3.89 (d, 1H, J=11 Hz), 3.03 (dt, 1H, J=8.1, 11 Hz), 2.07 (m, 1H), 2.02 (m, 1H), 1.88 (m, 2H), 1.78 (m, 2H), 1.39 (t, 3H, J=7.1 Hz).

Preparation of i-5d

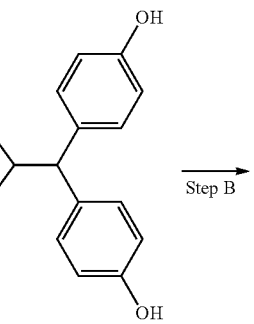

i-5a

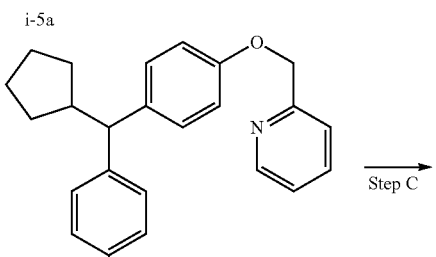

i-5b

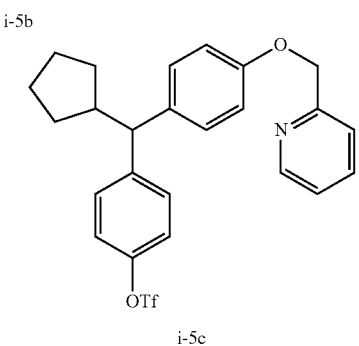

i-5c

Step A: Preparation of 4,4'-(cyclopentylmethylene)diphenol (i-5a)

Chlorotrimethylsilane (1.50 mL, 11.8 mmol) was added to a stirred solution of cyclopentanecarboxaldehyde (1.00 g, 10.2 mmol), phenol (2.90 g, 30.8 mmol) and 3-mercaptopropionic acid (87.0 μL, 1.00 mmol). The resulting mixture was heated to 65 for 2 h. After cooling to room temperature, the reaction mixture was poured into 0.1N HCl and extracted three times with EtOAc. The combined organic extracts were washed with water, brine, dried (Na$_2$SO$_4$) and concentrated in vacuo. Purification of the crude residue by flash chromatography on silica gel (gradient elution; 10%-20% EtOAc/hexanes as eluent) afforded the title compound i-5a. $^1$HNMR (500 MHz, CDCl$_3$): δ 7.14 (d, 4H, J=8.5 Hz), 6.73 (d, 4H, J=8.7 Hz), 3.47 (d, 1H, J=11.2 Hz), 2.58 (m, 1H), 1.64 (m, 4H), 1.55 (m, 2H), 1.14 (m, 2H).

Step B: Preparation of 4-{cyclopentyl[4-(pyridin-2-ylmethoxy)phenyl]methyl}phenol (i-5b) (Formula Ia wherein R¹ is —OH, R² is -Cyclopentyl, R³ is —H)

Cesium carbonate (2.20 g, 6.75 mmol), potassium iodide (1.10 g, 6.63 mmol) and 2-picolyl chloride hydrochloride (1.10 g, 6.71 trump) were added to a stirred solution of i-5a (1.80 g, 6.71 mmol) in DMF (25 mL). After approximately 20 h, the reaction was quenched by the addition of saturated aqueous ammonium chloride. The resulting mixture was extracted three times with EtOAc. The combined organic extracts were washed with water, brine, dried ($Na_2SO_4$) and concentrated in vacuo. Purification of the crude residue by flash chromatography on silica gel (gradient elution; 15%-40% EtOAc/hexanes as eluent) afforded the title compound i-5b. m/z (ES) 360 (MH)$^+$. $^1$HNMR (500 MHz, CDCl$_3$): δ 8.60 (d, 1H, J=4.9 Hz), 7.75 (m, 1H), 7.56 (d, 1H, J=8.0 Hz), 7.26 (m, 1H), 7.18 (d, 2H, J=8.7 Hz), 7.13 (d, 2H, J=8.7 Hz), 6.89 (d, 2H, J=8.4 Hz), 6.73 (d, 2H, J=8.4 Hz), 5.19 (s, 2H), 3.47 (d, 1H, J=11 Hz), 2.60 (m, 1H), 1.50-1.70 (m, 6H), 1.14 (m, 2H).

Step C: Preparation of 4-{cyclopentyl[4-(pyridin-2-ylmethoxy)phenyl]methyl}phenyl trifluoromethanesulfonate (i-5c) (Formula Ia wherein R¹ is —OTf, R² is -cyclopentyl, R³ is —H)

Lithium bis(trimethylsilyl)amide (2.20 mL of a 1.0 M solution in THF, 2.20 mmol) was added to a stirred solution of i-5b (650 mg, 1.81 mmol) in THF (18 mL) at 0° C. After 5 min, N-phenyltrifluoroxnethanesulfonimide (790 mg, 2.21 mmol) was added, and the resulting mixture stirred at (1° C. for 20 min. The reaction mixture was poured into water and extracted three times with EtOAc. The combined organic extracts were washed with water, brine, dried ($Na_2SO_4$) and concentrated in vacuo. Purification of the crude residue by flash chromatography on silica gel (gradient elution; 10%-30% EtOAc/hexanes as eluent) afforded the title compound i-5c. m/z (ES) 492 (MH)$^+$.

Step D: Preparation of methyl 4-{cyclopentyl[4-(pyridin-2-ylmethoxy)phenyl]methyl}benzoate (i-5d) (Formula Ia wherein R¹ is —CO₂Me, R² is -cyclopentyl, R³ is —H)

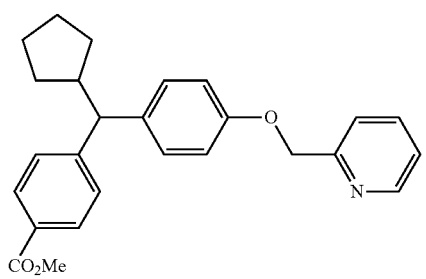

i-5d

Palladium (II) acetate (76.0 mg, 0.339 mmol) and 1,1'-bis(diphenylphosphino)ferrocene (280 mg, 0.505 mmol) were added successively to a solution of i-5c (840 mg, 1.71 moot) in triethylamine:DMF:methanol (30 mL of a 1:10:10 mixture, respectively). The reaction mixture was saturated with carbon monoxide and then heated to 80° C. under a carbon monoxide atmosphere (balloon) for 16 h. After cooling to room temperature, the reaction mixture was poured into 0.1N HCl (aq) and extracted three times with EtOAc. The combined organic extracts were washed with water, brine, dried ($Na_2SO_4$) and concentrated in vacuo. Purification of the crude residue by flash chromatography on silica gel (gradient elution; 10%-30% EtOAc/hexanes as eluent) afforded the title compound i-5d. m/z (ES) 492 (MH)$^+$. $^1$HNMR (500 MHz, CDCl$_3$): δ 8.64 (d, 1H, J=3.9 Hz), 7.93 (d, 2H, J=8.5 Hz), 7.91 (m, 1H), 7.69 (d, 1H, J=7.8 Hz), 7.40 (m, 1H), 7.34 (d, 2H, J=8.3 Hz), 7.21 (d, 2H, J=8.4 Hz), 6.92 (d, 2H, J=8.7 Hz), 5.32 (s, 2H), 3.89 (s, 3H), 3.60 (d, 1H, J=11.2 Hz), 2.68 (m, 1H), 1.53-1.72 (m, 6H), 1.16 (m, 2H).

Preparation of i-5e and i-5f

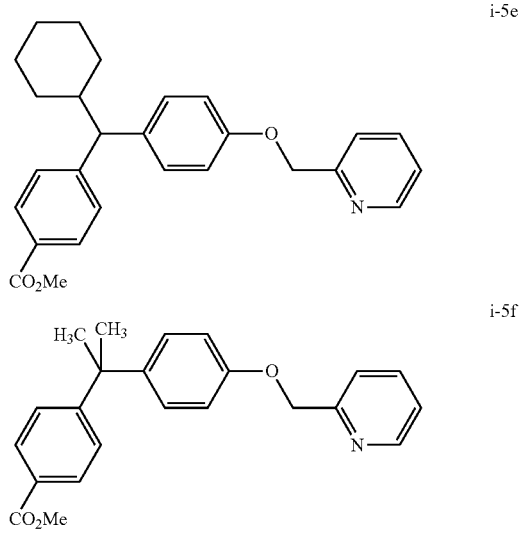

i-5e and i-5f were prepared from cyclohexanecarboxaldehyde and acetone, respectively, in place of cyclopentanecarboxaldehyde following the procedures as described above for making i-5d.

Intermediate i-5e: m/z (ES) 416 (MH)$^+$. $^1$HNMR (500 MHz, CDCl$_3$): δ 8.63 (d, 1H, J=2.8 Hz), 7.94 (d, 2H, J=8.3 Hz), 7.88 (dd, 1H, J=7.6, 7.7 Hz), 7.67 (d, 1H, J=8.0 Hz), 738 (dd, 1H, J=5.2, 6.7 Hz), 7.33 (d, 2H, J=8.5 Hz), 7.20 (d, 2H, J=8.5 Hz), 6.92 (d, 2H, J=8.4 Hz), 5.30 (s, 2H), 3.88 (s, 3H), 3.51 (d, 1H, J=10.7 Hz), 2.09 (m, 1H), 1.66 (m, 4H), 1.20 (m, 4H), 0.87 (m, 2H).

Intermediate i-5f: m/z (ES) 362 (MH)$^+$. $^1$HNMR (500 MHz, CDCl$_3$): δ 8.62 (d, 1H, J=4.4 Hz), 7.95 (d, 2H, J=8.5 Hz), 7.76 (dt, 1H, J=1.4, 7.8 Hz), 7.57 (d, 1H, J=7.8 Hz), 7.32 (d, 2H, J=8.5 Hz), 7.26 (dd, 1H, J=5.9, 6.0 Hz), 7.15 (d, 2H, J=8.9 Hz), 6.93 (d, 2H, J=8.9 Hz), 5.22 (s, 2H), 3.92 (s, 3H), 1.70 (s, 6H).

Preparation of i-6d

Step A: Preparation of ethyl 4-[(1-methylcyclopropyl)carbonyl]benzoate (i-6a)

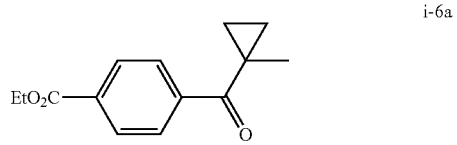 [SMILES: CCOC(=O)c1ccc(C(=O)C2(C)CC2)cc1]

i-6a

Lithium bis(trimethylsilyl)amide (8.60 mL of a 1.0 M solution in THF, 8.60 mmol) was added dropwise to a stirred solution of i-3a (1.70 g, 7.79 mmol) in THF (40 mL) at −78° C. After 10 min, iodomethane (0.590 mL, 9.48 mmol) was added, and the resulting mixture was allowed to warm to room temperature over 4 h. After another 10 h, the reaction mixture was quenched by addition of saturated aqueous ammonium chloride and extracted twice with EtOAc. The combined organic extracts were washed with 1 N HCl, brine, dried (Na$_2$SO$_4$) and concentrated in vacuo. Purification of the crude residue by flash chromatography on silica gel (gradient elution; 0%-10% EtOAc/hexanes as eluent) afforded the title compound i-6a. m/z (ES) 233 (MH)$^+$. $^1$HNMR (500 MHz, CDCl$_3$): δ 8.13 (d, 2H, J=8.2 Hz), 7.80 (d, 2H, J=8.2 Hz), 4.43 (q, 2H, J=7.1 Hz), 1.45 (s, 3H), 1.44 (t, 3H, J=7.1 Hz), 1.35 (m, 2H), 0.87 (m, 2H).

Steps B-D: Preparation of ethyl 4-{(1-methylcyclopropyl)[4-(pyridin-2-ylmethoxy)phenyl]methyl}benzoate (i-6d)

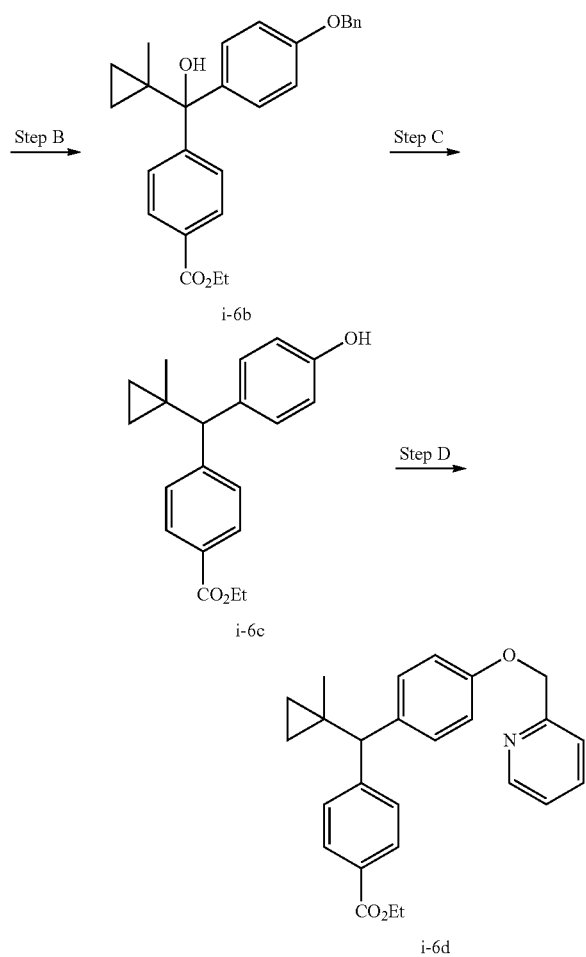

Intermediates i-6b, i-6c and i-6d were prepared from i-6a following the above procedures as described for intermediates i-4-b through i-4-d. For i-6d: m/z (ES) 402 (MH)$^+$. $^1$HNMR (500 MHz, CDCl$_3$): δ 8.61 (d, 1H, J=4.6 Hz), 7.97 (d, 2H, J=8.4 Hz), 7.73 (dt, 1H, J=1.6, 7.8 Hz), 7.57 (d, 1H, J=7.8 Hz), 7.34 (d, 2H, J=8.5 Hz), 7.26 (m, 1H), 7.14 (d, 2H, J=8.7 Hz), 6.92 (d, 2H, J=8.7 Hz), 5.22 (s, 2H), 4.38 (q, 2H, J=7.1 Hz), 3.83 (s, 1H), 1.41 (t, 3H, J=7.1 Hz), 1.09 (s, 3H), 0.46 (m, 4H).

Preparation of ethyl 4-{(1-methylcyclobutyl)[4-(pyridin-2-ylmethoxy)phenyl]methyl}benzoate (i-6e)

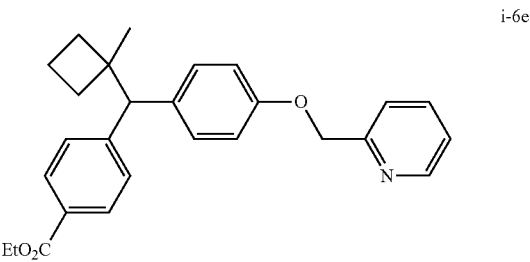 [SMILES: CCOC(=O)c1ccc(C(c2ccc(OCc3ccccn3)cc2)C2(C)CCC2)cc1]

Intermediate i-6e was prepared from i-4a following the procedures as described above for making i-6d. m/z (ES) 416 (MH)$^+$. $^1$HNMR (500 MHz, CDCl$_3$): δ 8.61 (d, 1H, J=5.6 Hz), 7.96 (d, 2H, J=8.2 Hz), 7.74 (dt, 1H, J=1.8, 7.7 Hz), 7.56 (d, 1H, J=8.1 Hz), 7.28 (d, 2H, J=8.5 Hz), 7.25 (m, 1H), 7.12 (d, 2H, J=8.7 Hz), 6.93 (d, 2H, J=8.7 Hz), 5.21 (s, 2H), 4.38 (q, 2H, J=7.1 Hz), 4.01 (s, 1H), 2.21 (m, 2H), 1.99 (m, 1H), 1.76 (m, 1H), 1.63 (m, 2H), 1.40 (t, 3H, J=7.1 Hz), 1.29 (s, 3H).

In the Tables in the following Examples, compounds having mass spectral data were synthetically prepared.

EXAMPLE 1

Preparation of (−)-5-(4-{2,2-dimethyl-1-[4-(pyridin-2-ylmethoxy)phenyl]propyl}phenyl)-1,3,4-oxadiazol-2-amine (1a)

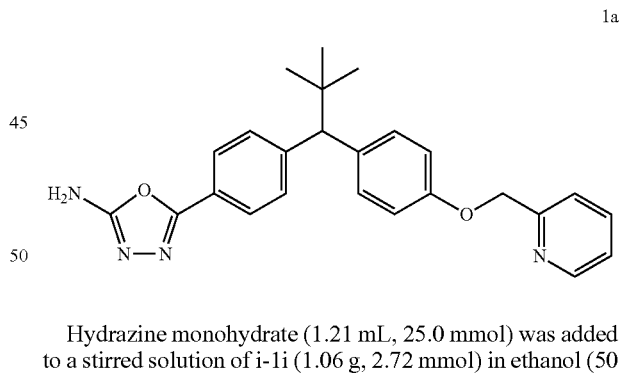

Hydrazine monohydrate (1.21 mL, 25.0 mmol) was added to a stirred solution of i-1i (1.06 g, 2.72 mmol) in ethanol (50 mL) and the resulting solution heated at reflux for 2.5 h. After cooling to room temperature, the volatiles were removed in vacuo, and the residue was partitioned between EtOAc, and water. The organic phase was separated, washed three times with water, brine, dried (MgSO$_4$) and concentrated in vacuo. The crude residue was dissolved in dioxane (30 mL) to which aqueous sodium bicarbonate (245 mg, 2.92 mmol in 7.0 mL of water) was added dropwise via syringe. A solution of cyanogen bromide (310 mg, 2.93 mmol) in dioxane (5.0 mL) was then added slowly, and the resulting mixture was aged at ambient temperature for approximately 18 h. The reaction mixture was poured into saturated aqueous sodium bicarbonate and extracted three times with EtOAc. The combined organic extracts were washed with brine, dried (MgSO₄) and concentrated in vacuo. Purification of the crude residue by flash chromatography on silica gel (gradient elution; 0%-100% EtOAc/hexanes as eluent) afforded the title compound 1a. m/z (ES) 415 (MH)⁺. ¹HNMR (500 MHz, CD₃OD): δ 8.53 (d, 1H, J=4.8 Hz), 7.85 (dt, 1H, J=1.6, 7.7 Hz), 7.79 (d, 2H, J=8.4 Hz), 7.58 (m, 3H), 7.40 (d, 2H, J=8.9 Hz), 7.35 (dd, 1H, J=5.2, 7.0 Hz), 6.94 (d, 2H, J=9.0 Hz), 5.15 (s, 2H), 3.81 (s, 1H), 1.02 (s, 9H).

The general procedure described above for making Compound 1a was also be performed using i-1h in place of i-1i to make (+) 5-(4-{2,2-dimethyl-1-[4-(pyridin-2-ylmethoxy)phenyl]propyl}-phenyl)-1,3,4-oxadiazol-2-amine.

Following procedures similar to that described above for making Compound 1a, the following compounds in Table I can be prepared:

TABLE 1

| Ex. #1 | R² | R³ |
|---|---|---|
| b | Me | H |
| c | Et | H |
| d | Pr | H |
| e | i-Pr | H |
| f | Cyclopropyl | H |
| g | Cyclobutyl | H |
| h | Cyclopentyl | H |
| i | Cyclohexyl | H |
| j | ⋈ (gem-dimethylcyclopropyl) | H |
| k | ⋈ (gem-dimethylcyclobutyl) | H |
| l | Me | Me |
| m | Et | Me |
| n | i-Pr | Me |
| o | t-Bu | Me |
| p | Cyclopropyl | Me |
| q | Cyclobutyl | Me |
| r | ⋈ (gem-dimethylcyclopropyl) | Me |
| s | (cyclobutyl) | Me |
| aa | C(Me)₂CF₃ | H |
| bb | C(Me)₂CF₂H | H |
| cc | i-Pr | OH |
| dd | t-Bu | OH |

Table 1 Parent Ion m/z (MH)⁺MS data for compounds:

1f: 5-(4-{cyclopropyl[4-(pyridin-2-ylmethoxy)phenyl]methyl}phenyl)-1,3,4-oxadiazol-2-amine, m/z (ES) 399 (MH)⁺, racemate was made.

1g: 5-(4-{cyclobutyl[4-(pyridin-2-ylmethoxy)phenyl]methyl}phenyl)-1,3,4-oxadiazol-2-amine, m/z (ES) 413 (MH)⁺, racemate, (+) and (−) enantiomers were made.

1j: 5-(4-{(1-methylcyclopropyl)[4-(pyridin-2-ylmethoxy)phenyl]methyl}phenyl)-1,3,4-oxadiazol-2-amine, m/z (ES) 413 (MH)⁺, racemate was made.

1k: 5-(4-{(1-methylcyclobutyl)[4-(pyridin-2-ylmethoxy)phenyl]methyl}phenyl)-1,3,4-oxadiazol-2-amine, m/z (ES) 427 (MH)⁺, racemate, (+) and (−) enantiomers were made.

aa: 5-(4-{3,3,3-trifluoro-2,2-dimethyl-1-[4-(pyridin-2-ylmethoxy)phenyl]propyl}phenyl)-1,3,4-oxadiazol-2-amine. m/z (ES) 469 (MH)⁺ racemate was made.

bb: 5-(4-{3,3-difluoro-2,2-dimethyl-1-[4-(pyridin-2-ylmethoxy)phenyl]propyl}phenyl)-1,3,4-oxadiazol-2-amine, m/z (ES) 451 (MH)⁺, racemate, (+) and (−) enantiomers were made.

1n: 5-(4-{1,2-dimethyl-1-[4-(pyridin-2-ylmethoxy)phenyl]propyl}phenyl)-1,3,4-oxadiazol-2-amine, m/z (ES) 415 (MH)⁺, (+) and (−) enantiomers were made.

cc: 1-[4-(5-amino-1,3,4-oxadiazol-2-yl)phenyl]-2-methyl-1-[4-(pyridin-2-ylmethoxy)phenyl]propan-1-ol, m/z (ES) 417 (MH)⁺, racemate was made.

dd: 1-[4-(5-amino-1,3,4-oxadiazol-2-yl)phenyl]-2,2-dimethyl-1-[4-(pyridin-2-ylmethoxy)phenyl]propan-1-ol, m/z (ES) 431 (MH)⁺; racemate was made.

Additionally, two anhydrous crystalline polymorphs (Form I and Form II) were identified for compound 1a. The X-ray powder diffraction pattern (FIG. 1) observed for Form I of compound 1a has characteristic diffraction peaks corresponding to d-spacings of 18.9, 6.3, 3.8, 3.7 and 3.4 angstroms. The X-ray powder diffraction pattern was generated on a Philips X'pert instrument. Cupper K-Alpha radiation was used as the source. The experiment was run at ambient condition.

Figure 2:
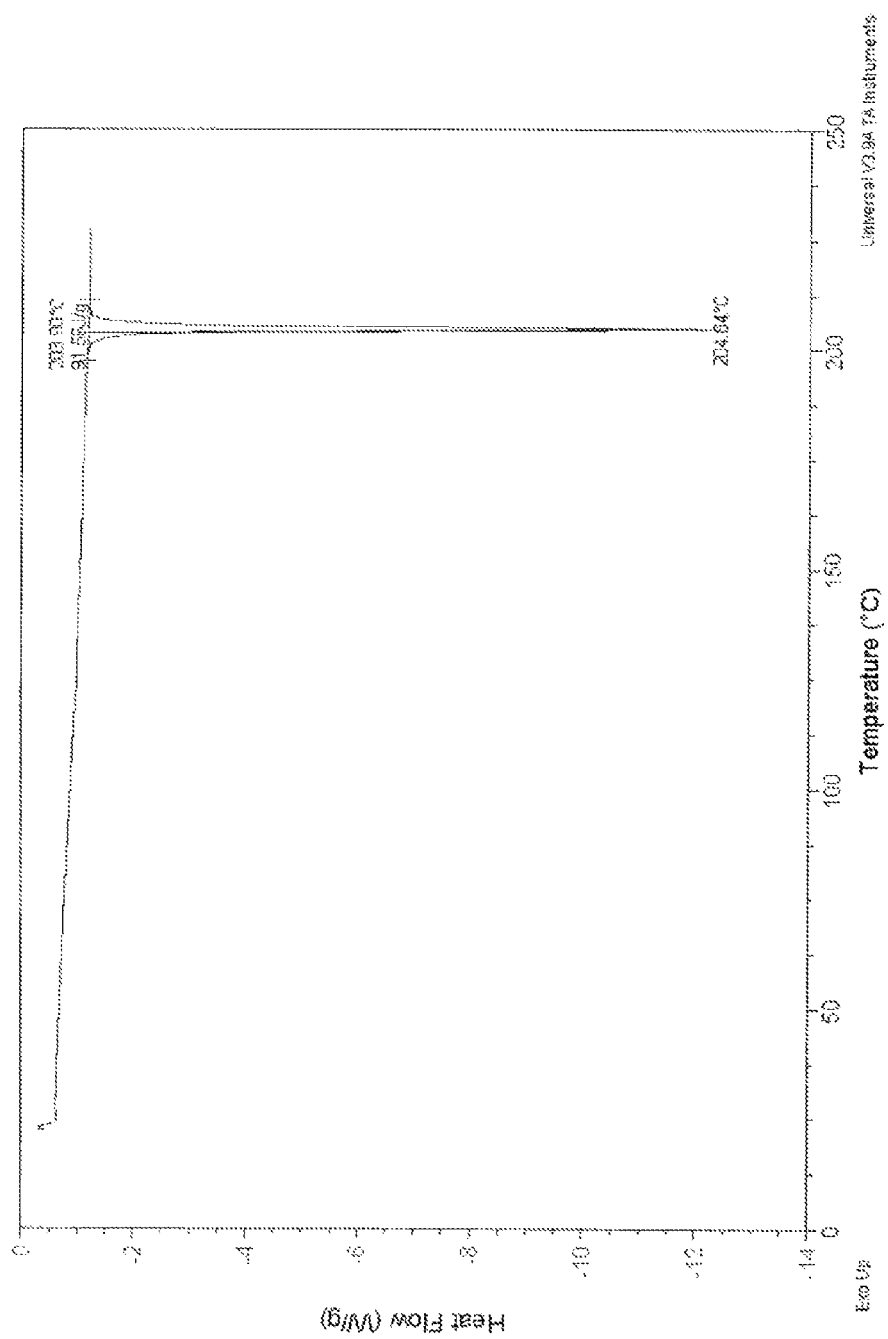

Differential scanning calorimetry (DSC) results for Form I of compound 1a (FIG. 2) were collected at a heating rate of 10° C./min, under nitrogen atmosphere in a closed pan. An endotherm due to melting was observed at an extrapolated onset temperature of 203.9° C.

Figure 3:
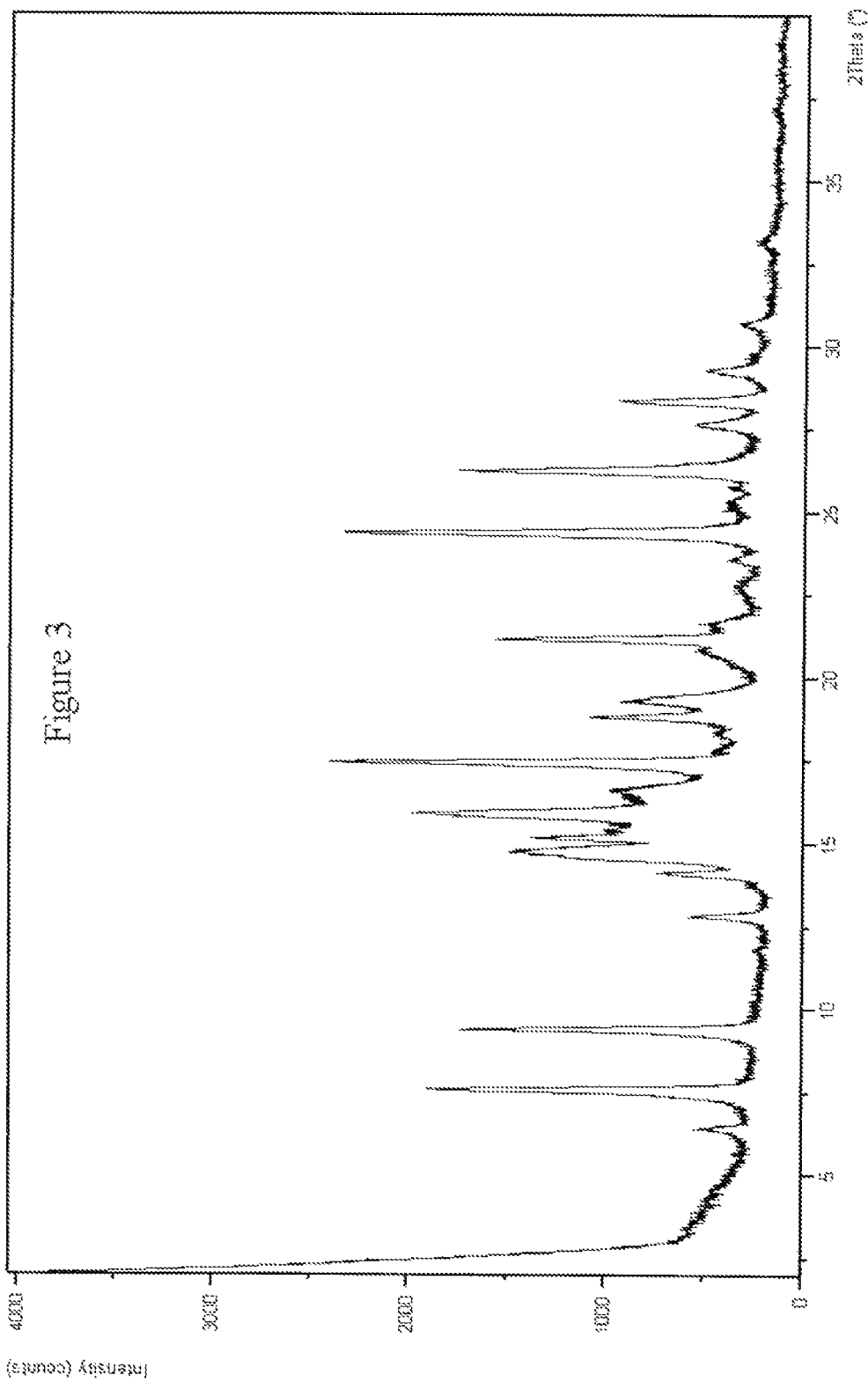

The X-ray powder diffraction pattern (FIG. 3) observed for Form II of compound 1a has characteristic diffraction peaks corresponding to d-spacings of 11.7, 9.4, 5.1, 3.7 and 3.4 angstroms. The X-ray powder diffraction pattern was generated on a Philips X'pert instrument. Cupper K-Alpha radiation was used as the source. The experiment was run at ambient condition.

Figure 4:
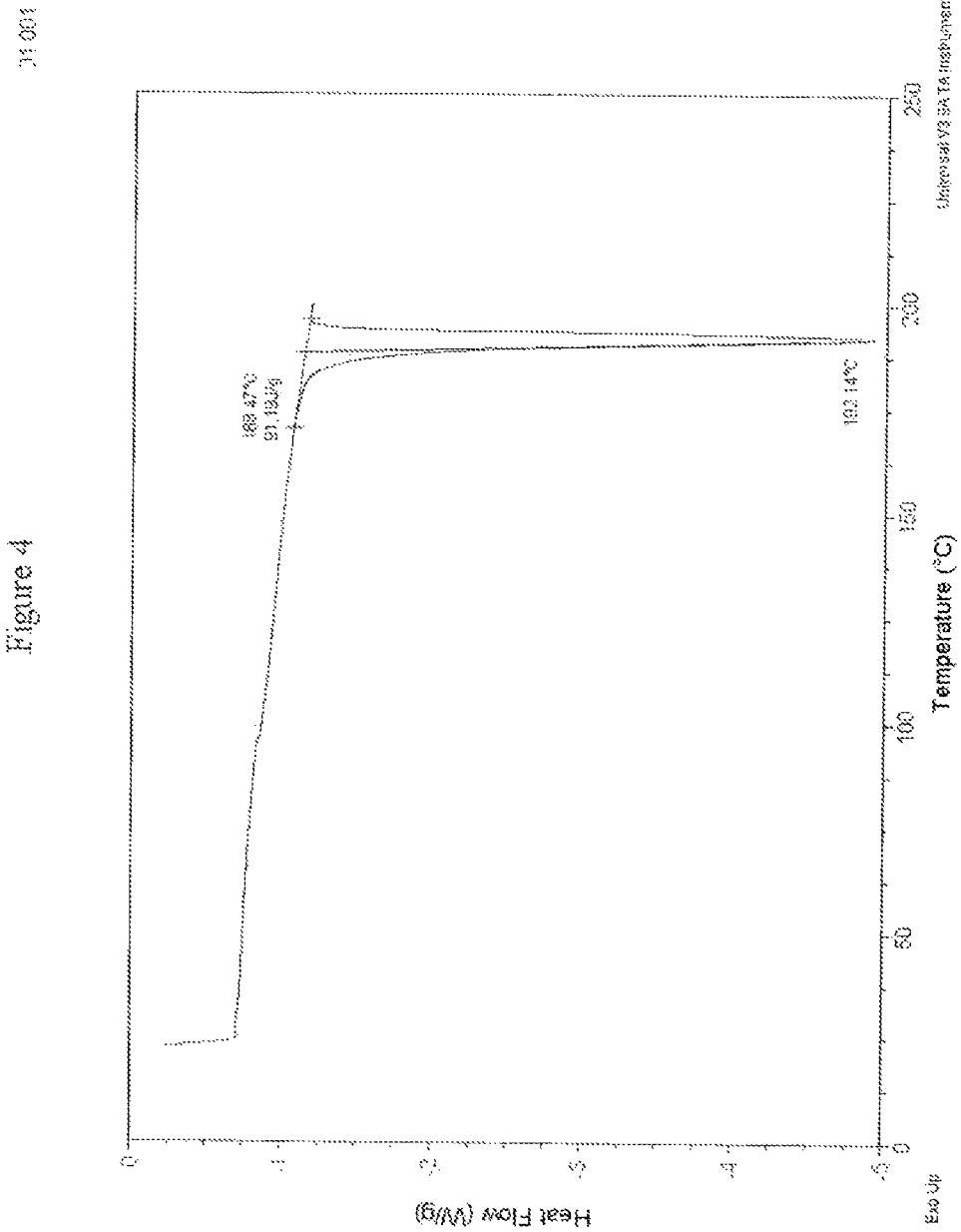

Differential scanning calorimetry (DSC) results for Form II of compound 1a (FIG. 4) were collected at a heating rate of 10° C./min, under nitrogen atmosphere in a closed pan. An endotherm due to melting was observed at an extrapolated onset temperature of 188.5° C.

In addition to the X-ray powder diffraction patterns described above, the crystalline forms of compound 1a was further characterized by solid-state carbon-13 nuclear magnetic resonance (NMR) spectra. The solid-state carbon-13 NMR spectrum was obtained on a Bruker DSX 400WB NMR system using a Broker 4 mm double resonance CPMAS probe. The carbon-13 NMR spectrum utilized proton/carbon-13 cross-polarization magic-angle spinning with variable-amplitude cross polarization. The sample was spun at 15.0 kHz, and a total of 1500 scans were collected with a recycle delay of 3 seconds. A line broadening of 40 Hz was applied to the spectrum before FT was performed. Chemical shifts are reported on the TMS scale using the carbonyl carbon of glycine (176.03 p.p.m.) as a secondary reference.

Figure 5:
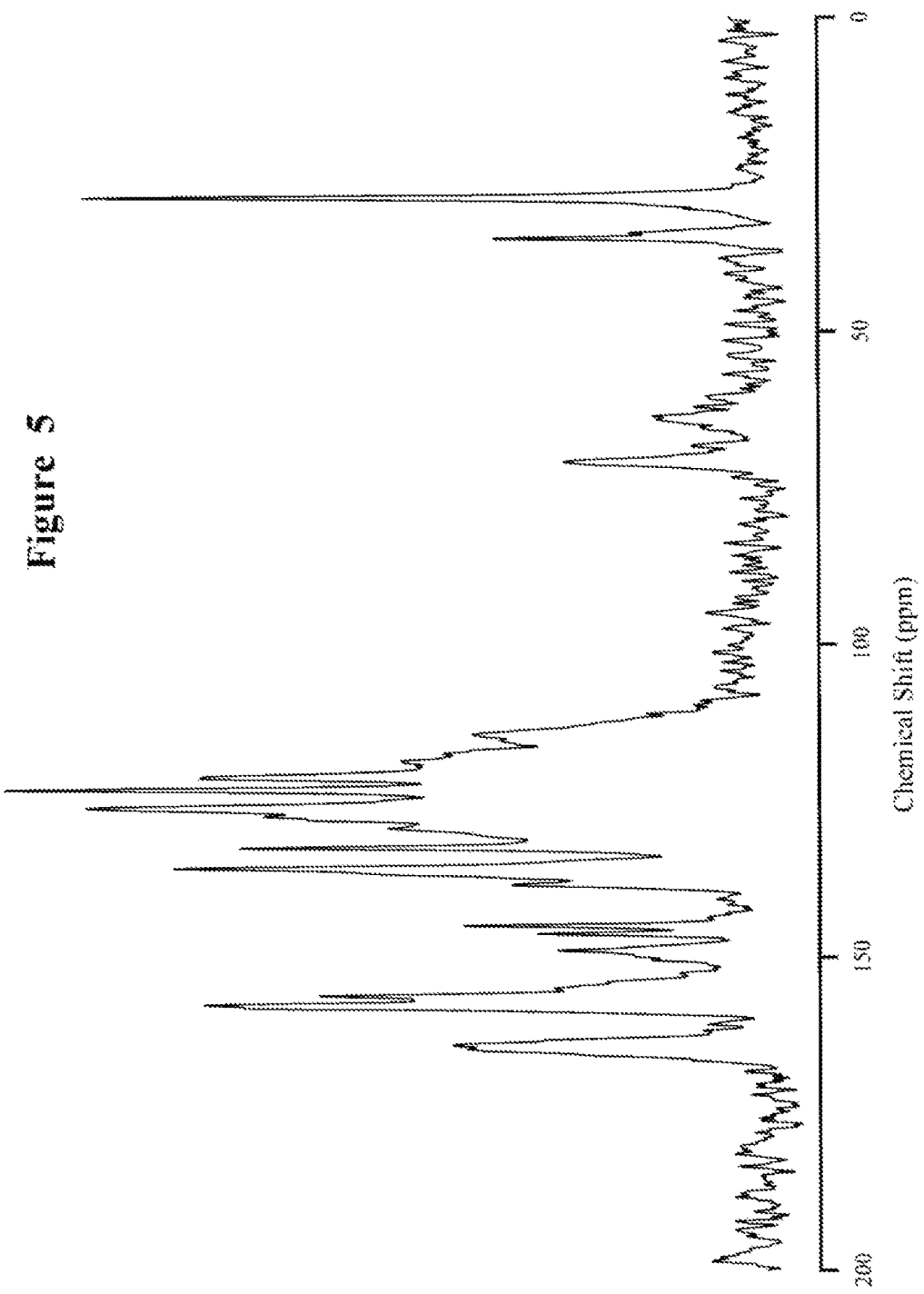

FIG. 5 shows the solid-state carbon-13 CPMAS NMR spectrum for Form I of compound 1a. Form I exhibited characteristic signals with chemical shift values of 28.7, 123.3, and 157.7 p.p.m. Further characteristic of Form I are the signals with chemical shift values of 35.2, 135.8, and 164.1 p.p.m. Form I is even further characterized by signals with chemical shift values of 70.9, and 145.0 p.p.m.

Figure 6:
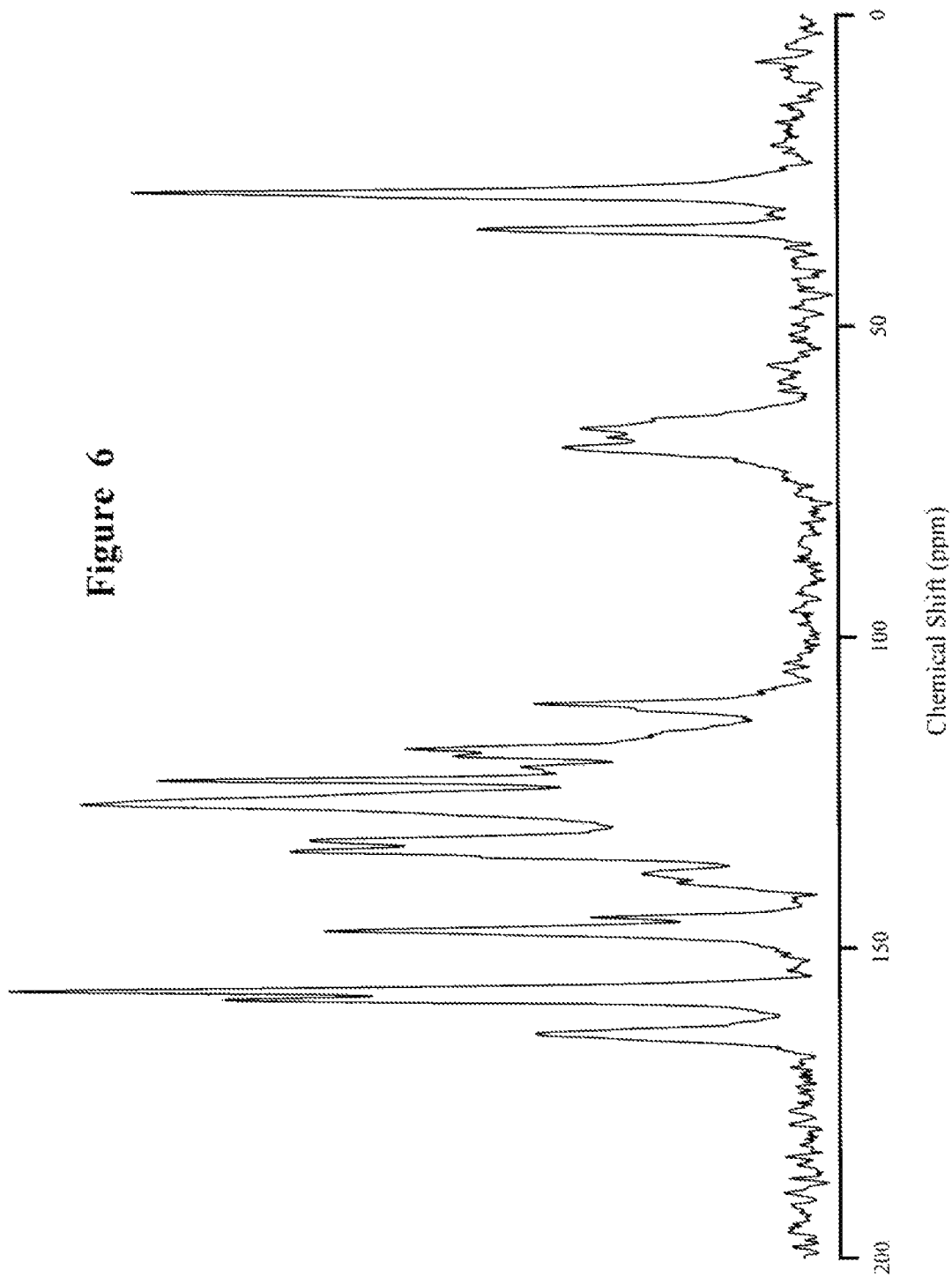

FIG. 6 shows the solid-state carbon-13 CPMAS NMR spectrum for Form II of compound 1a. Form II exhibited characteristic signals with chemical shift values of 28.4, 110.7, and 147.2 p.p.m. Further characteristic of Form II are the signals with chemical shift values of 34.3, 123.0, and 158.8 p.p.m. Form II is even further characterized by signals with chemical shift values of 126.8 and 163.7 p.p.m.

EXAMPLE 2

Step A: Preparation of 4-{2,2-dimethyl-1-[4-(pyridin-2-ylmethoxy)phenyl]propyl}benzoic acid (2a)
(Formula Ia wherein $R^2$ is t-butyl, $R^3$ is —H and $R^1$ is —COOH Lithium hydroxide monohydrate (162 mg, 3.86 mmol) was added to i-1i (600 mg, 1.54 mmol) in dioxane:$H_2O$ (15 mL of a 2:1 mixture), and the resulting mixture was heated to 55° C. After 1 h, the reaction mixture was cooled to room temperature, quenched with 0.5 N hydrochloric acid and extracted three times with EtOAc. The combined organic extracts were washed successively with water, brine, dried ($Na_2SO_4$) and concentrated in vacuo to afford the title compound 2a.

Step B: Preparation of 4-{2,2-dimethyl-1-[4-(pyridin-2-ylmethoxy)phenyl]propyl}benzamide (2b)
(Formula Ia wherein $R^2$ is t-butyl, $R^3$ is —H and $R^1$ is —CONH$_2$)

Ammonium chloride (706 mg, 13.2 mmol), HATU (502 mg, 1.32 mmol) and DIPEA (2.50 mL, 14.1 mmol) were added to a stirred solution of 2a (330 mg, 0.880 mmol) in DMF (4.0 mL) at room temperature. After approximately 1 h, the reaction mixture was diluted with EtOAc and washed three times with water, saturated aqueous sodium bicarbonate, dried ($Na_2SO_4$) and concentrated in vacuo. Purification of the crude residue by flash chromatography on silica gel (gradient elution; 0%-100% EtOAc/hexanes as eluent) afforded the title compound 2b. m/z (ES) 375 (MH)$^+$. $^1$HNMR (500 MHz, CDCl$_3$): δ 8.59 (d, 1H, J=4.6 Hz), 7.73-7.69 (m, 3H), 7.52 (d, 1H, J=8.0 Hz), 7.49 (d, 2H, J=8.2 Hz), 7.33 (d, 2H, J=8.6 Hz), 7.23 (dd, 1H, J=5.3, 6.8 Hz), 6.92 (d, 2H, J=8.6 Hz), 6.18-6.02 (br m, 2H), 5.18 (s, 2H), 3.74 (s, 1H), 1.02 (s, 9H).

Step C: Preparation of 4-{2,2-dimethyl-1-[4-(pyridin-2-ylmethoxy)phenyl]propyl}-benzonitrile (2c)
(Formula Ia wherein $R^2$ is t-butyl, $R^3$ is —H and $R^1$ is —CN)

Cyanuric chloride (170 mg, 0.923 mmol) was added to a stirred solution of 2b (280 mg, 0.748 mmol) in DMF (5.0 mL). After 30 min, the reaction mixture was cooled to 0° C. and quenched with saturated aqueous sodium bicarbonate. The reaction mixture was extracted three times with EtOAc and the combined organic extracts were washed twice with water, saturated aqueous sodium bicarbonate, dried ($Na_2SO_4$) and concentrated in vacuo. Purification of the crude residue by flash chromatography on silica gel (gradient elution; 0%-40% EtOAc/hexanes as eluent) afforded the title compound 2c. in m/z (ES) 357 (MH)$^+$. $^1$HNMR (500 MHz, CDCl$_3$): δ 8.61 (d, 1H, J=4.5 Hz), 7.73 (dt, 1H, J=1.8, 7.8 Hz), 7.58 (d, 2H, J=8.3 Hz), 7.53 (m, 31), 7.32 (d, 2H, J=8.7 Hz), 7.25 (dd, 1H, J=5.2, 7.3 Hz), 6.95 (d, 2H, J=8.7 Hz), 5.20 (s, 2H), 3.75 (s, 1H), 1.03 (s, 9H).

Step D: Preparation of 2-[(4-{2,2-dimethyl-1-[4-(1H-tetrazol-5-yl)phenyl]propyl}phenoxy)methyl]pyridine ammoniate (2d)

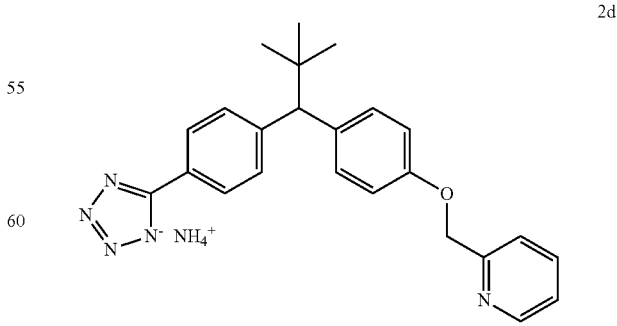

2d

Azidotrimethyltin (1.45 g, 7.04 mmol) was added to a stirred solution of 2c (626 mg, 1.76 mmol) in toluene (15 mL)

and the resulting solution heated to reflux for approximately 18 h. After cooling to room temperature, the reaction mixture was partially concentrated and diluted with ethanol. Hydrochloric acid (4 N in dioxane) was added, and after 1 h of vigorous agitation, the volatiles were removed in vacuo and the crude residue purified by flash chromatography on silica gel (gradient elution; 0%-100% DCM:methanol:ammonium hydroxide (85:15:1)/DCM as eluent) to afford the title compound 2d. $^1$HNMR (500 MHz, CD$_3$OD): δ 8.53 (d, 1H, J=4.8 Hz), 7.92 (d, 2H, J=8.3 Hz), 7.86 (dt, 1H, J=1.6, 7.6 Hz), 7.68 (d, 2H, J=8.3 Hz), 7.60 (d, 1H, J=7.8 Hz), 7.43 (d, 2H, J=8.7 Hz), 7.37 (dd, 1H, J=4.8, 7.0 Hz), 6.95 (d, 2H, J=8.7 Hz), 5.16 (s, 2H), 3.85 (s, 1H), 1.04 (s, 9H).

Step E: Preparation of 2-[(4-{2,2-dimethyl-1-[4-(2-methyl-2H-tetrazol-5-yl)phenyl]propyl}-phenoxy)methyl]pyridine (2e) and 2-[(4-{2,2-dimethyl-1-[4-(1-methyl-1H-tetrazol-5-yl)phenyl]propyl}phenoxy)methyl]pyridine (2f)

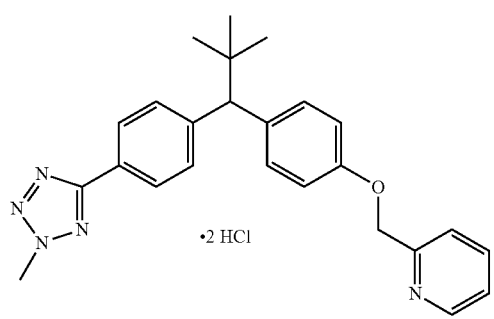

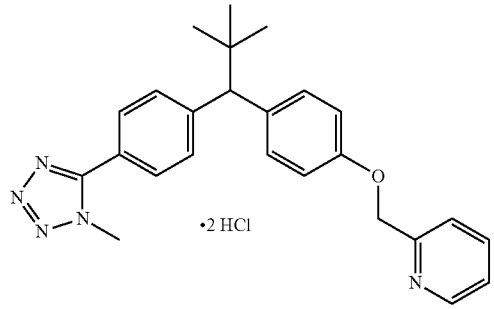

Iodomethane (67.0 μL, 1.08 mmol) was added to a stirred suspension of cesium carbonate (701 mg, 2.15 mmol) and 2d (224 mg, 0.538 mmol) in DMF (5 mL) at room temperature. After 2 μl, the reaction mixture was poured into saturated aqueous sodium bicarbonate and extracted three times with ethyl acetate. The combined organic extracts were washed twice with water, brine, dried (Na$_2$SO$_4$) and concentrated in vacuo. Purification of the crude residue by flash chromatography on silica gel (gradient elution; 10%-30% EtOAc/hexanes as eluent) afforded in order of elution, the title compounds 2e and 2f.

Compound 2e was treated with hydrogen chloride (saturated solution in EtOAc) and concentrated in vacuo. The resulting product was triturated with ether, and lyophilized from acetonitrile:H$_2$O to afford 2e: 2HCl. 2e: m/z (ES) 414 (MH)$^+$. $^1$HNMR (500 MHz, CD$_3$OD): δ 8.81 (d, 1H, J=6.0 Hz), 8.58 (m, 1H), 8.13 (d, 1H, J=8.5 Hz), 8.00 (d, 2H, J=8.3 Hz), 7.99 (m, 1H), 7.62 (d, 2H, J=8.3 Hz), 7.50 (d, 1H, ,J=8.9 Hz), 7.06 (d, 2H, J=8.7 Hz), 5.48 (s, 2H), 4.41 (s, 3H), 3.86 (s, 1H), 1.05 (s, 9H).

In a similar manner to that described above, compound 2f was converted to 2f: 2HCl: m/z (ES) 414 (MH)$^+$. $^1$HNMR (500 MHz, CD$_3$OD): δ 8.79 (d, 1H, J=5.0 Hz), 7.52 (t, 1H, J=7.8 Hz), 8.08 (d, 1H, J=8.0 Hz), 7.94 (dd, 1H, J=6.0, 7.5 Hz), 7.40 (m, 4H), 7.51 (d, 2H, J=9.0 Hz), 7.06 (d, 2H, J=8.5 Hz), 5.45 (s, 2H), 4.19 (s, 3H), 3.92 (s, 1H), 1.06 (s, 9H).

Following procedures similar to that described above for making Compounds 2e and 2f and procedures similar to that described in Example 6, the following compounds in Table 2 can be prepared:

TABLE 2

Id $$\text{structure with } R^2, R^3, R^6$$

and

Ie $$\text{structure with } R^2, R^3, R^6$$

| Compound No. | | | | |
|---|---|---|---|---|
| Id | Ie | R$^2$ | R$^3$ | R$^6$ |
| 2g) | 2g) | i-Pr | H | Me |
| 2h) | 2h) | Cyclopropyl | H | Me |
| 2i) | 2i) | Cyclobutyl | H | Me |
| 2j) | 2j) | ⋈ (gem-dimethylcyclopropyl) | H | Me |
| 2k) | 2k) | ⋈ (cyclobutyl-spiro) | H | Me |
| 2l) | 2l) | i-Pr | Me | Me |
| 2m) | 2m) | t-Bu | Me | Me |
| 2n) | 2n) | Cyclopropyl | Me | Me |
| 2o) | 2o) | Cyclobutyl | Me | Me |
| 2p) | 2p) | ⋈ | Me | Me |

TABLE 2-continued

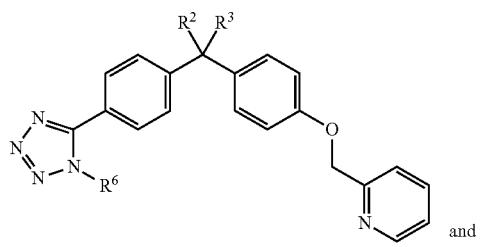
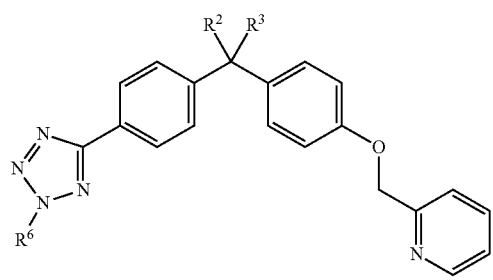

| Compound No. | | | | |
|---|---|---|---|---|
| Id | Ie | R² | R³ | R⁶ |
| 2q) | 2q) | (cyclobutyl) | Me | Me |
| 2r) | 2r) | i-Pr | H | Et |
| 2s) | 2s) | t-Bu | H | Et |
| 2t) | 2t) | Cyclopropyl | H | Et |
| 2u) | 2u) | Cyclobutyl | H | Et |
| 2v) | 2v) | (cyclopropyl) | H | Et |
| 2w) | 2w) | (cyclobutyl) | H | Et |
| 2x) | 2x) | i-Pr | Me | Et |
| 2y) | 2y) | t-Bu | Me | Et |
| 2z) | 2z) | Cyclopropyl | Me | Et |
| 2aa) | 2aa) | Cyclobutyl | Me | Et |
| 2ab) | 2ab) | (cyclopropyl) | Me | Et |
| 2ac) | 2ac) | (cyclobutyl) | Me | Et |

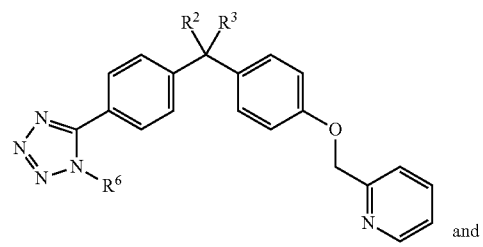
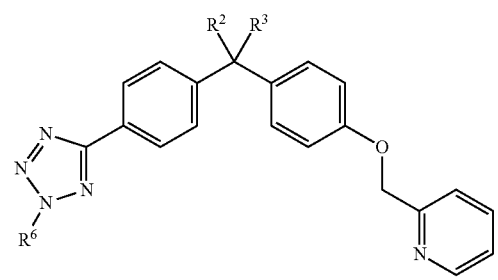

| Compound No. | | | | |
|---|---|---|---|---|
| Id | Ie | R² | R³ | R⁶ |
| 2ad) | 2ad) | i-Pr | H | i-Pr |
| 2ae) | 2ae) | t-Bu | H | i-Pr |
| 2af) | 2af) | Cyclobutyl | H | i-Pr |
| 2ag) | 2ag) | (cyclopropyl) | H | i-Pr |
| 2ah) | 2ah) | (cyclobutyl) | H | i-Pr |
| 2ai) | 2ai) | i-Pr | Me | i-Pr |
| 2aj) | 2aj) | t-Bu | Me | i-Pr |
| 2ak) | 2ak) | Cyclobutyl | Me | i-Pr |
| 2al) | 2al) | (cyclopropyl) | Me | i-Pr |
| 2am) | 2am) | (cyclobutyl) | Me | i-Pr |
| 2an) | 2an) | i-Pr | H | CHF₂ |
| 2ao) | 2ao) | t-Bu | H | CHF₂ |
| 2ap) | 2ap) | cyclobutyl | H | CHF₂ |
| 2aq) | 2aq) | (cyclopropyl) | H | CHF₂ |

TABLE 2-continued
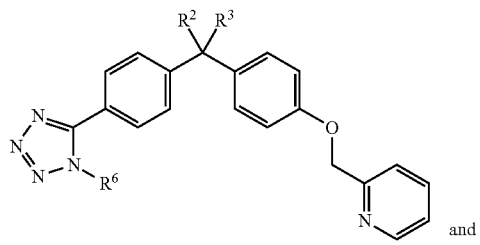
Id
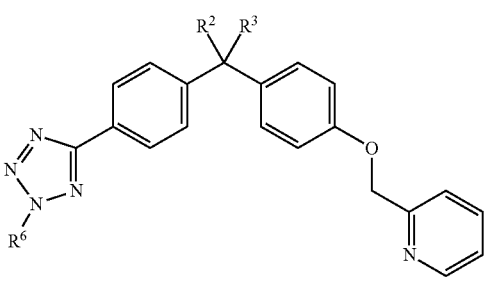
Ie
Compound No.
| Id | Ie | R² | R³ | R⁶ |
|---|---|---|---|---|
| 2ar) | 2ar) | 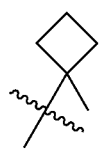 [SMILES: *C1(C)CCC1] | H | CHF₂ |
| 2as) | 2as) | i-Pr | Me | CHF₂ |
| 2at) | 2at) | t-Bu | Me | CHF₂ |
| 2au) | 2au) | i-Pr | H | 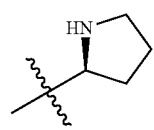 [SMILES: *[C@@H]1CCCN1] |
| 2av) | 2av) | t-Bu | H | 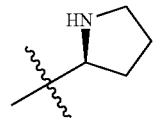 [SMILES: *[C@@H]1CCCN1] |
| 2aw) | 2aw) | cyclobutyl | H | 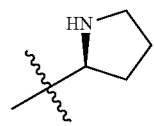 [SMILES: *[C@@H]1CCCN1] |
| 2ax) | 2ax) | 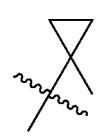 | H | 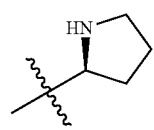 [SMILES: *[C@@H]1CCCN1] |
| 2ay) | 2ay) | 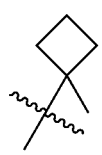 [SMILES: *C1(C)CCC1] | H | 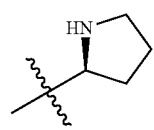 [SMILES: *[C@@H]1CCCN1] |
TABLE 2-continued
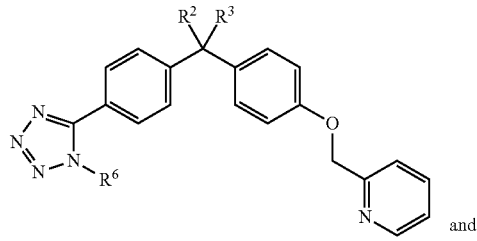
Id
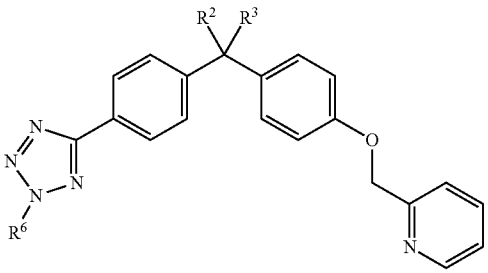
Ie
Compound No.
| Id | Ie | R² | R³ | R⁶ |
|---|---|---|---|---|
| 2az) | 2az) | i-Pr | Me | 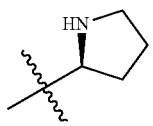 [SMILES: *[C@@H]1CCCN1] |
| 2ba) | 2ba) | t-Bu | Me | 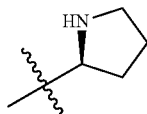 |
| 2bb) | 2bb) | i-Pr | H | 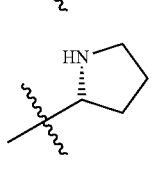 |
| 2bc) | 2bc) | t-Bu | H | 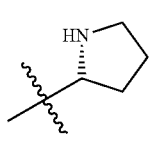 |
| 2bd) | 2bd) | cyclobutyl | H | 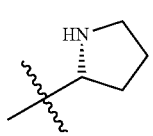 |
| 2be) | 2be) |  | H | 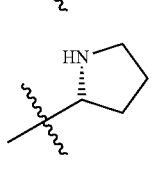 |
| 2bf) | 2bf) |  | H | 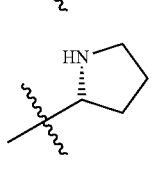 |

TABLE 2-continued
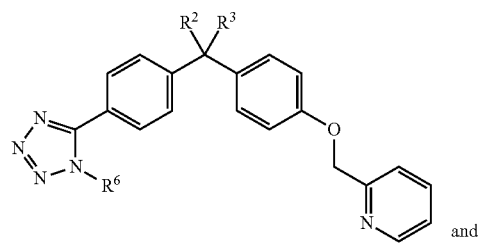
Id
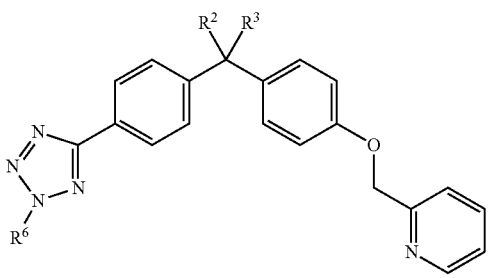
Ie
Compound No.
| Id | Ie | R² | R³ | R⁶ |
|---|---|---|---|---|
| 2bg) | 2bg) | i-Pr | Me | 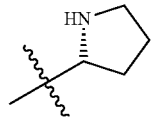 |
| 2bh) | 2bh) | t-Bu | Me | 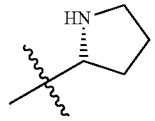 |
| 2bi) | 2bi) | i-Pr | H | 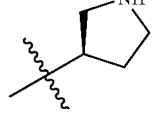 |
| 2bj) | 2bj) | t-Bu | H | 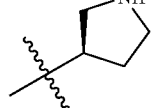 |
| 2bk) | 2bk) | cyclobutyl | H | 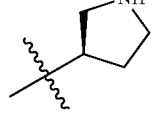 |
| 2bl) | 2bl) | 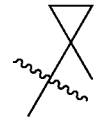 | H | |
| 2bm) | 2bm) | 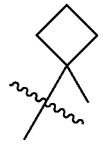 [SMILES: *C1(C)CCC1] | H | |
TABLE 2-continued
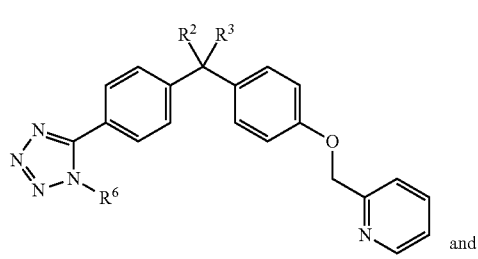
Id
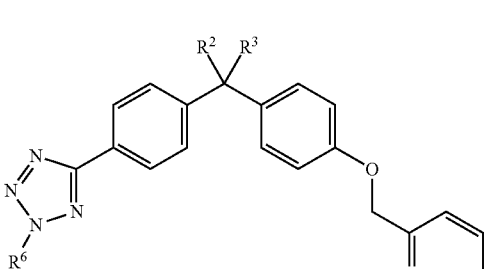
Ie
Compound No.
| Id | Ie | R² | R³ | R⁶ |
|---|---|---|---|---|
| 2bn) | 2bn) | i-Pr | Me | 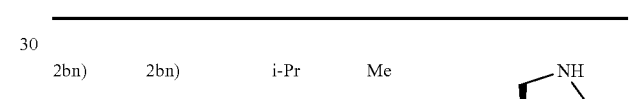 |
| 2bo) | 2bo) | t-Bu | Me |  |
| 2bp) | 2bp) | i-Pr | H | 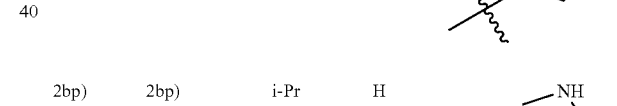 |
| 2bq) | 2bq) | t-Bu | H | 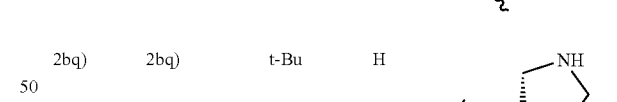 |
| 2br) | 2br) | cyclobutyl | H | 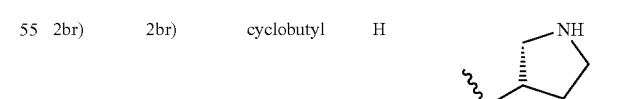 |
| 2bs) | 2bs) | H | |  |

TABLE 2-continued

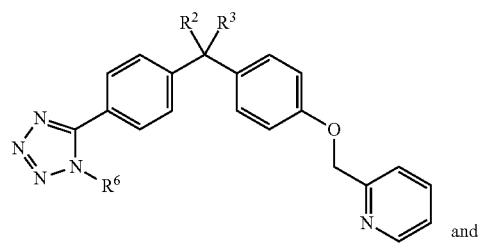

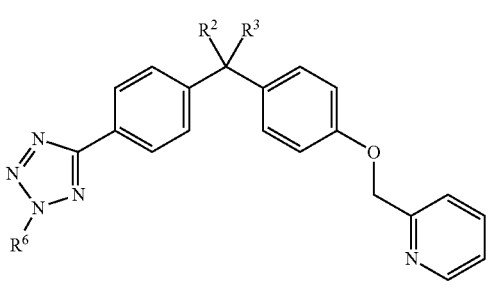

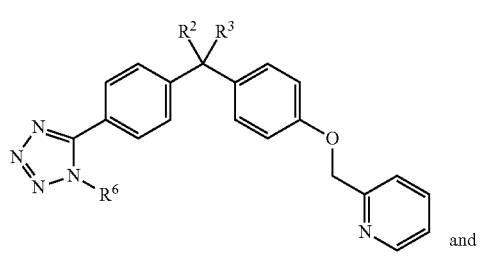

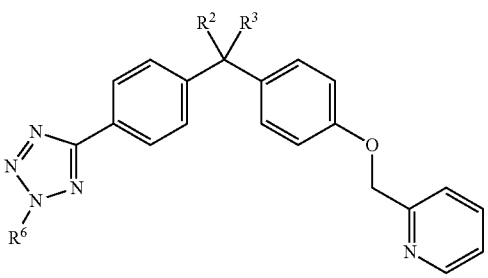

Compound No.

| Id | Ie | R² | R³ | R⁶ |
|---|---|---|---|---|
| 2bt) | 2bt) | (1-methylcyclobutyl) | H | (pyrrolidin-3-yl) |
| 2bu) | 2bu) | i-Pr | Me | (pyrrolidin-3-yl) |
| 2bv) | 2bv) | t-Bu | Me | (pyrrolidin-3-yl) |
| 2bw) | 2bw) | i-Pr | H | (piperidin-4-yl) |
| 2bx) | 2bx) | t-Bu | H | (piperidin-4-yl) |
| 2by) | 2by) | cyclobutyl | H | (piperidin-4-yl) |
| 2bz) | 2bz) | (1-methylcyclopropyl) | H | (piperidin-4-yl) |
| 2ca) | 2ca) | (1-methylcyclobutyl) | H | (piperidin-4-yl) |
| 2cb) | 2cb) | i-Pr | Me | (piperidin-4-yl) |
| 2cc) | 2cc) | t-Bu | Me | (piperidin-4-yl) |

Table 2 Parent Ion m/z (MH)⁺ MS data for compounds:
Id-2g: 2-[(4(4-{2-methyl-1-[4-(2-methyl-2H-tetrazol-5-yl)phenyl]propyl}phenoxy)methyl]pyridine, m/z (ES) 400 (MH)+, (+) and (−) enantiomers were made.
Ie-2g: 2-[(4-{2-methyl-1-[4-(1-methyl-1H-tetrazol-5-yl)phenyl]propyl}phenoxy)methyl]pyridine, m/z (ES) 400 (MH)+, (+) and (−) enantiomers were made.
The following compounds of Table 2 were made using intermediate i-2d:
Id-2l: 2-[(4-{1,2-dimethyl-1-[4-(1-methyl-1H-tetrazol-5-yl)phenyl]propyl}phenoxy)methyl]pyridine, m/z (ES) 414 (MH)+;
Ie-2l: 2-[4-{1,2-dimethyl-1-[4-(2-methyl-2H-tetrazol-5-yl)phenyl]propyl}phenoxy)methyl]pyridine, m/z (ES) 414 (MH)+, Id-2x: 2-[(4-{1-[4-(1-ethyl-1H-tetrazol-5-yl)phenyl]-1,2-dimethylpropyl}phenoxy)methyl]pyridine, m/z (ES) 428 (MH)+; and Ie-2x: 2-[(4-{1-[4-(2-ethyl-2H-tetrazol-5-yl)phenyl]-1,2-dimethylpropyl}phenoxy)methyl]pyridine, m/z (ES) 428 (MH)+;)+.

The following compounds of Table 2 were made using intermediate 1-1i:

Id-2s: 2-[(4-{1-[4-(1-ethyl-1H-tetrazol-5-yl)phenyl]-2,2-dimethylpropyl}phenoxy)methyl]pyridine, m/z (ES) 428 (MH)+;

Ie-2s: 2-[(4-{1-[4-(2-ethyl-2H-tetrazol-5-yl)phenyl]-2,2-dimethylpropyl}phenoxy)methyl]pyridine, m/z (ES) 428 (MH)+;

Ie-2av: 2-({4-[2,2-dimethyl-1-(4-{2-[(2S)-pyrrolidin-2-ylmethyl]-2H-tetrazol-5-yl}phenyl)propyl]phenoxy}methyl)pyridine, m/z (ES) 483 (MH)+;

Ie-2bc: 2-({4-[2,2-dimethyl-1-(4-{2-[(2S)-pyrrolidin-2-ylmethyl]-2H-tetrazol-5-yl}phenyl)propyl]phenoxy}methyl)pyridine, m/z (ES) 483 (MH)+;

Ie-2bj: 2-({4-[2,2-dimethyl-1-(4-{2-[(3R)-pyrrolidin-2-ylmethyl]-2H-tetrazol-5-yl}phenyl)propyl]phenoxy}methyl)pyridine, m/z (ES) 483 (MH)+;

Ie-2bq: 2-({4-[2,2-dimethyl-1-(4-{2-[(3S)-pyrrolidin-2-ylmethyl]-2H-tetrazol-5-yl}phenyl)propyl]phenoxy}methyl)pyridine, m/z (ES) 483 (MH)+; and Ie-2bx: 2-{[4-(2,2-dimethyl-1-{4-[2-(piperidin-4-ylmethyl)-2H-tetrazol-5-yl]phenyl}propyl)phenoxy]methyl}pyridine, m/z (ES) 497 (MH)+.

EXAMPLE 3

Step A: Preparation of methyl 4-{2,2-dimethyl-1-[4-(1-pyridin-2-ylpropoxy)phenyl]propyl}benzoate (3a)

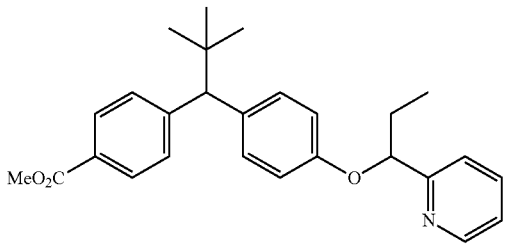

3a

Cesium carbonate (715 mg, 2.19 mmol), and 2-(1-bromopropyl)pyridine (165 mg, 0.825 mmol) were added to a stirred solution of i-1g (165 mg, 0.553 mmol) in DMF (2.0 mL) at room temperature. After 5 min, the resulting mixture was heated to 60° C. and stirred vigorously for approximately 2 h. After cooling to room temperature, the reaction mixture was filtered, washed with DMF (1.0 mL) and poured into a vigorously stirred solution of ice cold brine. A gummy residue precipitated out of solution which was isolated by decanting the supernatant. The crude gum was purified by flash chromatography on silica gel (isocratic elution; 10% EtOAc/hexanes as eluent) to afford the title compound 3a.

Step B: Preparation of (3b) and (3c)

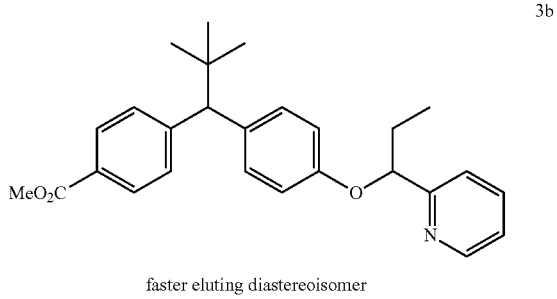

3b faster eluting diastereoisomer

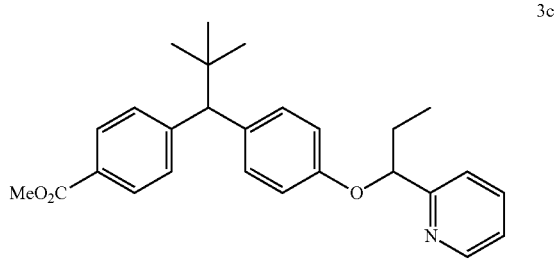 [SMILES: CCC(Oc1ccc(C(c2ccc(C(=O)OC)cc2)C(C)(C)C)cc1)c1ccccn1]

3c slower eluting diastereoisomer

Diastereoisomers 3b and 3c were separated using preparative chiral supercritical fluid chromatography (Chiralpak® AD-H stationary phase, 250×20 mm column dimensions, 40% methanol/$CO_2$ as eluent at 50 mL/min, 100 bar outlet pressure with UV detection at 220 nm). The faster eluting diastereoisomer 3b had a retention time of ~4.6 min and the slower eluting enantiomer 3c had a retention time of ~8.4 min. The eluants were concentrated to provide:

3b: m/z (ES) 417 (MH)+. $^1$HNMR (500 MHz, CDCl$_3$): δ 8.58 (d, J=5.0 Hz, 1H), 7.91 (d, 2H, J=8.7 Hz), 7.62 (m, 1H), 7.44 (d, 2H, J=8.7 Hz), 7.37 (d, 1H, J=5 Hz), 7.21 (d, 2H, J=8.7 Hz), 7.18 (m, 1H), 6.77 (d, 2H, J=8.7 Hz), 5.13 (dd, 1H, J=5.2, 6.3 Hz), 3.89 (s, 3H), 3.68 (s, 1H), 2.00 (m, 2H), 1.04 (t, 3H, J=7.4 Hz), 0.98 (s, 9H).

3c: m/z (ES) 417 (MH)+. $^1$HNMR (500 MHz, CDCl$_3$): δ 8.59 (t, 1H, J=2.6 Hz), 7.93 (m, 2H), 7.63 (m, 1H), 7.46 (d, 2H, J=8.7 Hz), 7.39 (m, 1H), 7.24 (d, 2H, J=8.0 Hz), 7.19 (m, 1H), 6.79 (d, 2H, J=8.7 Hz), 5.15 (m, 1H), 3.90 (s, 3H), 3.69 (s, 1H), 2.01 (m, 2H), 1.05 (t, 3H, J=7.3 Hz), 0.99 (s, 9H).

Step C: Preparation of 4-{2,2-dimethyl-1-[4-(1-pyridin-2-ylpropoxy)phenyl]propyl}benzo-hydrazide (3d)

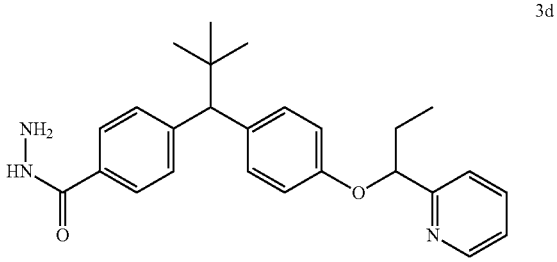 [SMILES: CCC(Oc1ccc(C(c2ccc(C(=O)NN)cc2)C(C)(C)C)cc1)c1ccccn1]

3d

Hydrazine monohydrate (364 mg, 3.79 mmol) was added to a solution of 3c (165 mg, 0.395 mmol) in ethanol (3.0 mL), and the resulting solution was heated at reflux for 8 h. After cooling to room temperature, the volatiles were removed in vacuo, and the crude residue was then coevaporated twice from toluene to afford the title compound 3d. m/z (ES) 417 (MH)$^+$. $^1$H NMR (500 MHz, CDCl$_3$) δ 8.58 (t, 1H, J=2.6 Hz), 7.63 (m, 2H), 7.57 (d, 2H, J=8.7 Hz), 7.37 (m, 1H), 7.30 (d, 2H, J=8.7 Hz), 7.19 (m, 1H), 7.06 (d, 2H, J=8.7 Hz), 6.49 (d, 2H, J=8.7 Hz), 5.13 (m, 1H), 3.8-4.3 (bs, 31), 3.69 (s, 1H), 2.00 (m, 2H), 1.05 (t, 3H, J=9.6 Hz), 1.0 (s, 9H).

Step C: Preparation of 5-(4-{2,2-dimethyl-1-[4-(1-pyridin-2-ylpropoxy)phenyl]propyl}phenyl)-1,3,4-oxadiazol-2-amine (3e)

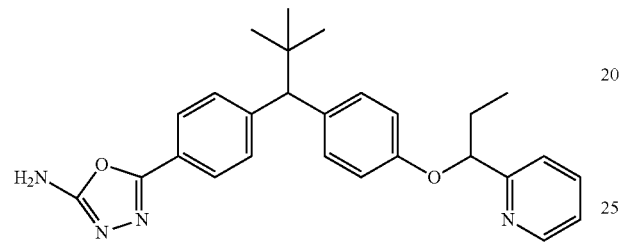

3e

Crude 3d (40.0 mg, 0.0967 mmol) was suspended in dioxane/water (1.3 mL of a 3:1 mixture) and cooled to approximately 5° C. A solution of aqueous sodium bicarbonate (22.0 mg, 0.237 mmol) in water (150 μL) was added followed by a solution of cyanogen bromide (15.0 mg, 0.142 mmol) in dioxane (100 μL). After 5 min, the reaction mixture was warmed to ambient temperature and aged for approximately 1 h. The reaction mixture was poured into saturated aqueous sodium bicarbonate/brine (1:1) and extracted twice with DCM. The combined organic extracts were dried (MgSO$_4$) and concentrated in vacuo. Purification of the crude residue by flash chromatography on silica gel (isocratic elution; 80% EtOAc/hexanes as eluent) afforded the title compound 3e. m/z (ES) 443 (M)$^+$. $^1$HNMR (500 MHz, CDCl$_3$): δ $^1$H NMR (500 MHz, CDCl$_3$) δ 8.61 (t, 1H, J==2.6 Hz), 7.79 (d, 2H, J=8.8 Hz), 7.66 (m, 1H), 7.48 (d, 2H, J=8.7 Hz), 7.40 (d, 1H, J=7.7 Hz), 7.25 (d, 2H, J=8.7 Hz), 7.20 (m, 1H), 6.81 (d, 2H, J=8.7 Hz), 5.5-5.8 (bs, 2H), 5.18 (t, 1H, J=6.9 Hz), 3.67 (s, 1H), 2.0 (m, 2H), 1.05 (t, 3H, J=7.3 Hz), 1.0 (s, 9H).

Following procedures similar to that described above for making Compound 3e, the following compounds in Table 3 can be prepared:

TABLE 3

| Ex. #3 | R$^2$ | R$^3$ | R$^4$ |
|---|---|---|---|
| f | i-Pr | H | Et |
| g | Cyclopropyl | H | Et |
| h | Cyclobutyl | H | Et |
| i | cyclopropyl (gem-disubst) | H | Et |
| j | cyclobutyl (gem-disubst) | H | Et |
| k | i-Pr | Me | Et |
| l | t-Bu | Me | Et |
| m | Cyclopropyl | Me | Et |
| n | Cyclobutyl | Me | Et |
| o | cyclopropyl (gem-disubst) | Me | Et |
| p | cyclobutyl (gem-disubst) | Me | Et |
| q | i-Pr | H | Me |
| r | t-Bu | H | Me |
| s | i-Pr | H | Me |
| t | t-Bu | H | Me |
| u | cyclopropyl (gem-disubst) | H | Me |
| v | cyclobutyl (gem-disubst) | H | Me |
| w | i-Pr | Me | Me |
| x | t-Bu | Me | Me |
| y | Cyclopropyl | Me | Me |
| z | Cyclobutyl | Me | Me |

TABLE 3-continued

Ig

![structure Ig]

| Ex. #3 | R² | R³ | R⁴ |
|---|---|---|---|
| aa | cyclopropyl | Me | Me |
| ab | cyclobutyl | Me | Me |

EXAMPLE 4

Step A: Preparation of 5-[4-(2,2-dimethyl-1-{4-[(1-oxidpyridin-2-yl)methoxy]phenyl}-propyl)phenyl]-1,3,4-oxadiazol-2-amine (4a)

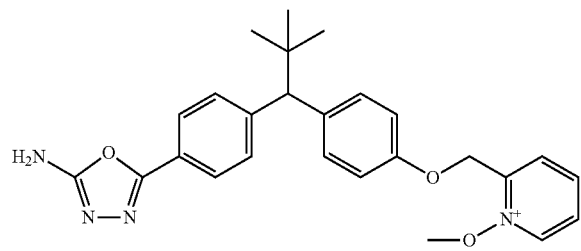

4a

3-Chloroperoxybenzoic acid (38 mg, 0.17 mmol) was added into a stirred solution of 1a (30.0 mg, 0.072 mmol) in DCM (1.0 ml) at room temperature and stirred for 1.75 h. The reaction mixture was then poured into saturated aqueous sodium bicarbonate and extracted three times with EtOAc. The combined organic extracts were washed twice with aqueous sodium sulfite (10% w/v), brine, dried ($Na_2SO_4$), and concentrated in vacuo. Purification of the crude residue by preparative reversed phase HPLC on YMC Pack Pro C18 stationary phase ($CH_3CN/H_2O$ as eluent, 0.05% TEA as modifier), followed by lyophilization of the purified fractions afforded the title compound 4a. m/z (ES) 431 (MH)⁺. ¹HNMR (500 MHz, $CD_3OD$): δ 8.37 (d, 1H, J=6.4 Hz), 7.79 (d, 2H, J=8.2 Hz), 7.69 (d, 1H, J=7.3 Hz), 7.60 (d, 2H, J=7.5 Hz), 7.57 (t, 1H, J=7.7 Hz), 7.46 (dd, 1H, J=6.1, 8.0 Hz), 7.41 (d, 2H, J=8.7 Hz), 6.96 (d, 2H, J=8.7 Hz), 5.28 (s, 2H), 3.81 (s, 1H), 1.00 (s, 9H).

Following procedures similar to that described above for making Compound 4a, the following compounds in Table 4 can be prepared:

TABLE 4

Ih

![structure Ih]

| Ex. #4 | R² | R³ |
|---|---|---|
| b | i-Pr | H |
| c | Cyclopropyl | H |
| d | Cyclobutyl | H |
| e | (1,1-cyclopropyl disubstituted) | H |
| f | (1,1-cyclobutyl disubstituted) | H |
| g | i-Pr | Me |
| h | t-Bu | Me |
| i | Cyclopropyl | Me |
| j | Cyclobutyl | Me |
| k | (1,1-cyclopropyl disubstituted) | Me |
| l | (1,1-cyclobutyl disubstituted) | Me |

EXAMPLE 5

Preparation of 5-(4-{2,2-dimethyl-1-[4-(1-methyl-1-pyridin-2-ylethoxy)phenyl]propyl}phenyl)-1,3,4-oxadiazol-2-amine (5h)

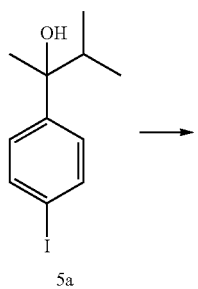

5a

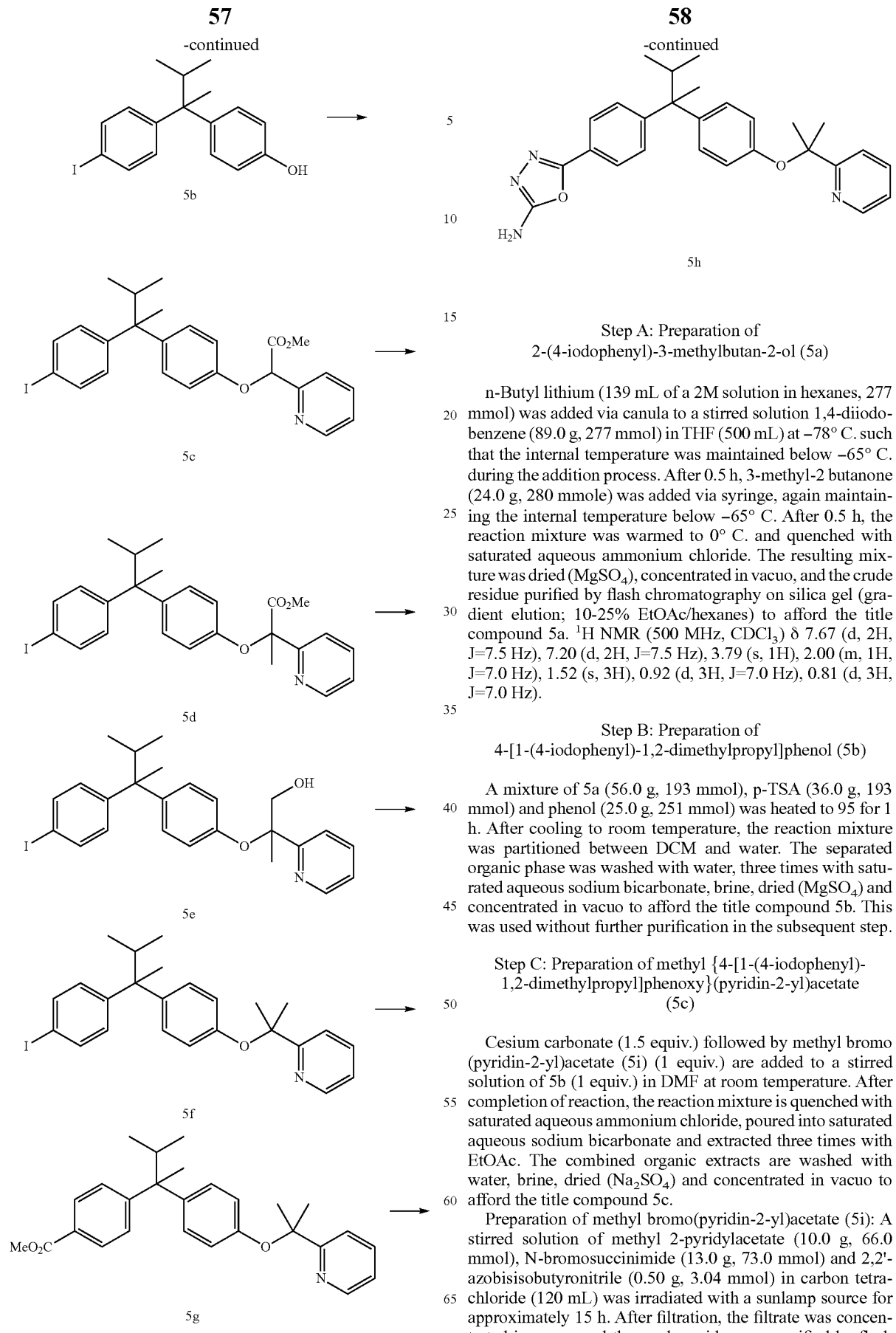

Step A: Preparation of 2-(4-iodophenyl)-3-methylbutan-2-ol (5a)

n-Butyl lithium (139 mL of a 2M solution in hexanes, 277 mmol) was added via canula to a stirred solution 1,4-diiodobenzene (89.0 g, 277 mmol) in THF (500 mL) at −78° C. such that the internal temperature was maintained below −65° C. during the addition process. After 0.5 h, 3-methyl-2 butanone (24.0 g, 280 mmole) was added via syringe, again maintaining the internal temperature below −65° C. After 0.5 h, the reaction mixture was warmed to 0° C. and quenched with saturated aqueous ammonium chloride. The resulting mixture was dried ($MgSO_4$), concentrated in vacuo, and the crude residue purified by flash chromatography on silica gel (gradient elution; 10-25% EtOAc/hexanes) to afford the title compound 5a. $^1$H NMR (500 MHz, $CDCl_3$) δ 7.67 (d, 2H, J=7.5 Hz), 7.20 (d, 2H, J=7.5 Hz), 3.79 (s, 1H), 2.00 (m, 1H, J=7.0 Hz), 1.52 (s, 3H), 0.92 (d, 3H, J=7.0 Hz), 0.81 (d, 3H, J=7.0 Hz).

Step B: Preparation of 4-[1-(4-iodophenyl)-1,2-dimethylpropyl]phenol (5b)

A mixture of 5a (56.0 g, 193 mmol), p-TSA (36.0 g, 193 mmol) and phenol (25.0 g, 251 mmol) was heated to 95 for 1 h. After cooling to room temperature, the reaction mixture was partitioned between DCM and water. The separated organic phase was washed with water, three times with saturated aqueous sodium bicarbonate, brine, dried ($MgSO_4$) and concentrated in vacuo to afford the title compound 5b. This was used without further purification in the subsequent step.

Step C: Preparation of methyl {4-[1-(4-iodophenyl)-1,2-dimethylpropyl]phenoxy}(pyridin-2-yl)acetate (5c)

Cesium carbonate (1.5 equiv.) followed by methyl bromo(pyridin-2-yl)acetate (5i) (1 equiv.) are added to a stirred solution of 5b (1 equiv.) in DMF at room temperature. After completion of reaction, the reaction mixture is quenched with saturated aqueous ammonium chloride, poured into saturated aqueous sodium bicarbonate and extracted three times with EtOAc. The combined organic extracts are washed with water, brine, dried ($Na_2SO_4$) and concentrated in vacuo to afford the title compound 5c.

Preparation of methyl bromo(pyridin-2-yl)acetate (5i): A stirred solution of methyl 2-pyridylacetate (10.0 g, 66.0 mmol), N-bromosuccinimide (13.0 g, 73.0 mmol) and 2,2'-azobisisobutyronitrile (0.50 g, 3.04 mmol) in carbon tetrachloride (120 mL) was irradiated with a sunlamp source for approximately 15 h. After filtration, the filtrate was concentrated in vacuo and the crude residue was purified by flash chromatography on silica gel (gradient elution; 5-10% EtOAc/hexane as eluent) to afford the title compound 5i.

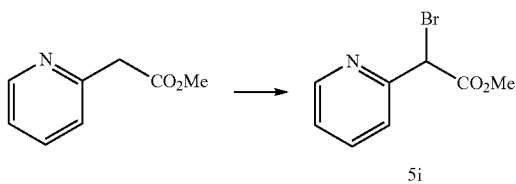 [SMILES: COC(=O)Cc1ccccn1 ; COC(=O)C(Br)c1ccccn1]

5i

Step D: Preparation of methyl 2-{4-[1-(4-iodophenyl)-1,2-dimethylpropyl]phenoxy}-2-pyridin-2-ylpropanoate (5d)

Lithium diisopropylamide mono (THF) (1.2 equiv. of a 5M solution in cyclohexane) is added to a stirred solution of 5c (1 equiv.) in THF at −78° C. After 15 mins, 1,3-dimethyl-3,4,5,6-tetrahydro-2(1H)-pyrimidinone (1 equiv.) is added followed by iodomethane (1.5 equiv). After 1 h, the reaction mixture is warmed to room temperature and aged until the reaction is deemed complete. The reaction mixture is quenched with saturated aqueous ammonium chloride, poured into saturated aqueous sodium bicarbonate and extracted three times with EtOAc. The combined organic extracts are washed with water, brine, dried ($Na_2SO_4$) and concentrated in vacuo. Purification of the crude residue by flash chromatography on silica gel affords the title compound 5d.

Step E: Preparation of 2-{4-[1-(4-iodophenyl)-1,2-dimethylpropyl]phenoxy}-2-pyridin-2-ylpropan-1-ol (5e)

Lithium borohydride (1 equiv) is added to a stirred solution of 5d (1 equiv) in THF at room temperature. After completion of reaction, the reaction mixture is quenched with 2 N HCl, poured into saturated aqueous sodium bicarbonate and extracted three times with EtOAc. The combined organic extracts are washed with water, brine, dried ($Na_2SO_4$) and concentrated in vacuo. Purification of the crude residue by flash chromatography on silica gel affords the title compound 5e.

Step F: Preparation of 2-(1-{4-[1-(4-iodophenyl)-1,2-dimethylpropyl]phenoxy}-1-methylethyl)pyridine (5f)

A solution of triflic anhydride (1 equiv.) in DCM is added to a solution of triphenylphosphine oxide (2 equiv) in DCM at 0° C. After precipitation is observed (~15 min), a solution of 5e (1 equiv) in DCM is added. After 5 min, sodium borohydride (4 equiv.) is added in one portion. After completion of reaction, the reaction mixture is quenched with 2 N HCl, poured into saturated aqueous sodium bicarbonate and extracted three times with EtOAc. The combined organic extracts are washed with water, brine, dried ($Na_2SO_4$) and concentrated in vacuo. Purification of the crude residue by flash chromatography on silica gel affords the title compound 5f.

Step G: Preparation of methyl 4-{1,2-dimethyl-1-[4-(1-methyl-1-pyridin-2-ylethoxy)phenyl]propyl}benzoate (5g)

A stirred mixture of 5f (1 equiv), palladium (II) acetate (0.1 equiv.), 1,1'bis(diphenylphosphino)ferrocene (0.2 equiv) and triethylamine (2.4 equiv) in DMF/methanol (1:1) is purged with carbon monoxide for approximately 10 min and then heated to 80° C. under a carbon monoxide atmosphere (balloon). After completion of reaction, the reaction mixture is cooled to room temperature and then filtered through a short column of CELITE®, eluting copiously with EtOAc. The filtrate is poured into saturated aqueous sodium bicarbonate and extracted three times with EtOAc. The combined organic extracts are washed with water, brine, dried ($Na_2SO_4$) and concentrated in vacuo. Purification of the crude residue by flash chromatography on silica gel affords the title compound 5g.

Step H: Preparation of 5-(4-{1,2-dimethyl-1-[4-(1-methyl-1-pyridin-2-ylethoxy)phenyl]propyl}phenyl)-1,3,4-oxadiazol-2-amine (5h)

Hydrazine monohydrate (10 equiv.) is added to a stirred solution of 5g (1 equiv.) in ethanol and the resulting solution heated at reflux until 5g is consumed. After cooling to room temperature, the volatiles are removed in vacuo, and the residue is partitioned between EtOAc and water. The organic phase is separated, washed three times with water, brine, dried ($MgSO_4$) and concentrated in vacuo. The crude residue is dissolved in dioxane to which aqueous sodium bicarbonate (1.1 equiv) in water is added dropwise via syringe. A solution of cyanogen bromide (1.1 equiv.) in dioxane is then added slowly, and the resulting mixture is aged at ambient temperature until the reaction is deemed complete. The reaction mixture is poured into saturated aqueous sodium bicarbonate and extracted three times with EtOAc. The combined organic extracts are washed with brine, dried ($MgSO_4$) and concentrated in vacuo. Purification of the crude residue by flash chromatography on silica gel affords the title compound 5h. If desired, 5h can be resolved into its enantiomeric components using preparative chiral HPLC techniques.

Following procedures similar to that described above for making Compound 5h, the following compounds in Table 5 can be prepared:

TABLE 5

| Ex. #5 | $R^2$ | $R^3$ |
|---|---|---|
| j | i-Pr | H |
| k | t-Bu | H |
| l | Cyclopropyl | H |
| m | Cyclobutyl | H |
| n | ⋈ | H |

TABLE 5-continued

Ii

| Ex. #5 | R² | R³ |
|---|---|---|
| o |  | H |
| p | t-Bu | Me |

EXAMPLE 6

Step A: Preparation of tert-butyl-4-{[5-(4-{2,2-dimethyl-1-[4-(pyridin-2-ylmethoxy)phenyl]propyl}phenyl)-2H-tetrazol-2-yl]methyl}piperidine-1-carboxylate (2h)

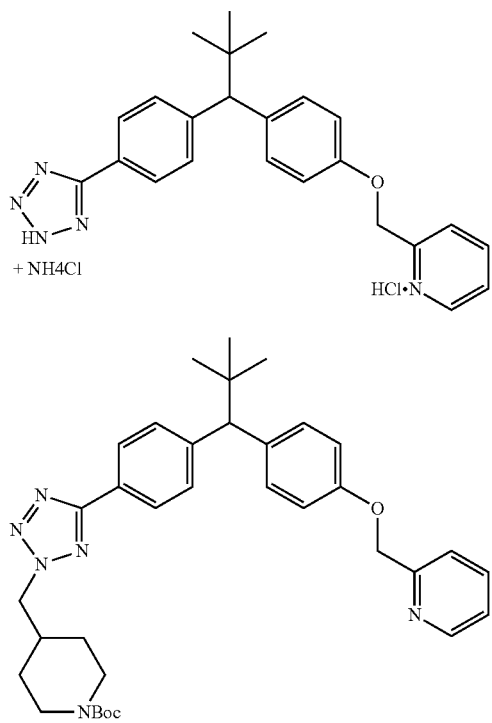

HCl (1M solution in ethanol; slight excess) was added to a solution of 2d (42.0 mg, 0.102 mmol) in EtOH (1.0 mL) at room temperature. After ~10 min, the resulting mixture was concentrated in vacuo to afford crude g. The residue was dissolved in DCM (1.5 mL), and to this solution was added N-Boc-4-piperidinemethanol (68.0 mg, 0.315 mmol), triphenylphosphine (132 mg, 0.505 mmol), and diethyl azodicarboxylate (80.0 µl, 0.511 mmol). After maintaining the reaction mixture at room temperature for 17 h, second portions of N-Boc-4-piperidinemethanal (68.0 mg, 0.315 mmol), triphenylphosphine (132 mg, 0.505 mmol), and diethyl azodicarboxylate (80.0 µl, 0.511 mmol) were added. The resulting solution was aged for another 5.5 µl, and then purified directly by flash chromatography on silica gel (gradient elution; 0%-50% EtOAc/hexanes as eluent) to afford 2h.

Step B: Preparation of 2-{[4-(2,2-dimethyl-1-{4-[2-(piperidin-4-ylmethyl)-2H-tetrazol-5-yl]phenyl}propyl)phenoxy]methyl}pyridine (compound Ie-2bx)

Ie-2bx

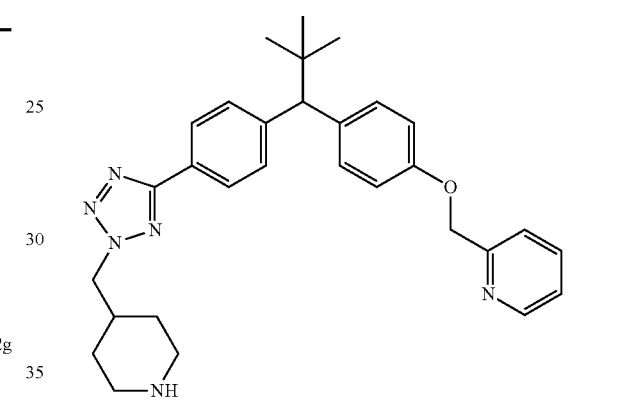

Crude 2h (0.102 mmol) was dissolved in a pre-mixed solution of 4N HCl in dioxane (5.00 mL) and deionized water (250 µL) at 10° C. The resultant solution was warmed to room temperature and aged for approximately 1.3 h. After concentrating in vacuo, the residue was purified by flash chromatography on silica gel [100% EtOAc (120 mL) followed by 0%-100% EtOAc/(DCM:MeOH:ammonium hydroxide (95:5:1)] to afford compound Ie-2bx, Ie-2bx: m/z (ES) 497 (MH)⁺. ¹HNMR (500 MHz, CDCl₃): δ 8.59 (d, 1H, J=4.3 Hz), 8.05 (d, 2H, J=8.2 Hz), 7.70 (dt, 1H, J=7.6, 1.4 Hz), 7.53 (m, 3H), 7.36 (d, 2H, J=8.7 Hz), 7.21 (dd, 1H, J=6.9, 5.1 Hz), 6.92 (d, 2H, J=8.4 Hz), 5.19 (s, 2H), 4.51 (d, 2H, J=7.1 Hz), 3.75 (s, 1H), 3.10 (bd, 2H, J=12.4 Hz), 2.60 (dt, 2H, J=12.1, 2.0 Hz), 2.21 (m, 1H), 1.86 (bs, 1H), 1.60 (bd, 2H, J=12.3 Hz), 1.28 (m, 2H), 1.04 (s, 9H).

EXAMPLE 7

7A) Preparation of Compound Ia, Polymorph Form II

Following essentially the same procedure as described in Example 1 for making compound 1a but omitting the flash chromatography step, crystalline Form II was obtained. Adding a flash chromatography purification step to this synthetic procedure is not expected to change the crystalline form (i.e., 1a Form II) thus obtained.

7B) Preparation of Compound Ia, Polymorph Form I 310 mg of Compound k crystalline Form II was dissolved in 5.0 ml of ethanol (water content unknown) by heating to 63° C. The mixture was cooled to ambient temperature at an approximate rate of 15° C. per hour. The slurry was then re-heated to 55° C. (solids did not completely dissolve) and cooled to room temperature (15° C./hour) twice. The crystals were collected by filtration and washed with recycled mother liquors. After drying, 220 mg of material was isolated and identified to be Form I.

Although the water content of the ethanol was unknown, addition of water, for example from 1% up to 20% water in alcohol v/v, can increase the rate of turnover of Form II to Form I.

7C) Preparation of Compound Ia, Polymorph Form I Using Seed 250 mg of Compound 1a crystalline Form II was dissolved in 2.5 ml of ethanol and 0.125 ml of water by heating to >60° C. The solution was cooled to 50° C. and seeded with Form I. The slurry was held at 50° C. and then cooled to 40° C. over ~1 h. 0.25 ml of water was added to the slurry and it was then reheated to 50° C. and then re-cooled to 40° C. twice and then held at 40° C. overnight (~18 h) at which point a sample of the solids were shown to be Form I by XRPD. The slurry was cooled to room temperature and held overnight. Isolation by filtration afforded Form I.

The addition of water, for example from 1% up to 20% water in an alcohol v/v, can increase the rate of turnover of Form II to Form I when following a seeded procedure as well as an unseeded procedure. The procedures described in examples 7B and 7C can also be performed using isopropanol in place of ethanol. Heating is an element of both seeded and unseeded procedures as well, and while Form I can be obtained using a broad range of temperatures, a temperature in the range from about 40° C. to 60° C. is preferred. However, temperatures outside this range can be used, as shown in examples 7B and 7C.

FLAP Binding Assay

Compound A

Compound B

A 100,000×g pellet from human leukocyte 10,000×g supernatants (1) is the source of FLAP. The 100,000×g pellet membranes were resuspended in Tris-Tween assay buffer (100 mM Tris HCl pH 7.4, 140 mM NaCl, 2 mM EDTA, 0.5 mM dithiothreitol, 5% glycerol, 0.05% Tween 20) to yield a final protein concentration of 50 µg to 150 µg/ml. Aliquots (100 µl) of membrane suspension were added to 12 mm×75 mm polypropylene tubes containing 100 µl Tris-Tween assay buffer, 30,000 cpm of Compound A in 5 µl MeOH:assay buffer (1:1), and 2 µl dimethyl sulfoxide or competitor (i.e., the compound to be tested) in dimethyl sulfoxide. Compound B (10 µM final concentration) was used to determine non-specific binding. After a 20 minute incubation at room temperature, tube contents were diluted to 4 ml with cold 0.1M Tris HCl pH 7.4, 0.05% Tween 20 wash buffer and the membranes were collected by filtration of GFB filters presoaked in the wash buffer. Tubes and filters were rinsed with 2×4 ml aliquots of cold wash buffer. Filters were transferred to 12 min×3.5 mm polystyrene tubes for determination of radioactivity by gamma-scintillation counting.

Specific binding is defined as total binding minus non-specific binding. Total binding was Compound A bound to membranes in the absence of competitor; non-specific binding was Compound A bound in the presence of 10 uM Compound B. Preparation of Compound A is described in reference 1, below. The $IC_{50}$ values were obtained by computer analysis (see reference 2, below) of the experimental data, Representative tested compounds of the invention were determined to have an $IC_{50}$<50 nM.

REFERENCES

1. Charleson, S., Prasti, P., Leger, S., Gillard, J. W, Vickers, P. J., Mancini, J. A., Charleson, P., Quay, J., Ford-Hutchinson, A. W., and Evans, J. F. (1992) Characterization of a 5-lipoxygenase-activating protein binding assay: correlation of affinity for 5-lipoxygenase-activating protein with leukotriene synthesis inhibition. Mal Pharmacol 41:873-879.

2. Kinetic, EBDA, Ligand, Lowry: A collection of Radioligand Binding Analysis Programs by G. A. McPherson. Elsevier-BIOSOFT.

While the invention has been described with reference to certain particular embodiments thereof, numerous alternative embodiments will be apparent to those skilled in the art from the teachings described herein. All patents, patent applications and publications cited herein are incorporated by reference in their entirety.

What is claimed is:

1. A compound represented by structural formula I

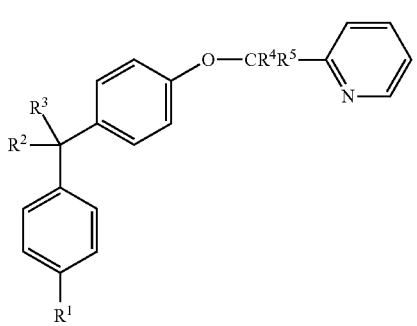

the pyridyl-N-oxide analog of formula I, or a pharmaceutically acceptable salt thereof wherein:

R¹ is

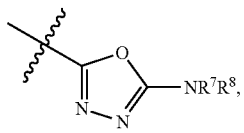

R² is selected from the group consisting of (a) —C₁₋₆ alkyl optionally substituted with 1-3 of fluoro, (b) —C₃₋₆ cycloalkyl and

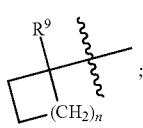

n is an integer selected from 0, 1, 2 and 3;
R³ is selected from the group consisting of —H, —F, —OH, —CH₃ and —CF₃;
R⁴ is selected from the group consisting of —H and —C₁₋₄alkyl;
R⁵ is selected from the group consisting of —H and —CH₃; and
R⁷ is selected from the group consisting of —H, —C₁₋₆alkyl optionally substituted with 1-3 fluoro, —C₃₋₆ cycloalkyl optionally substituted with 1-3 fluoro, —COC₁₋₆alkyl and —COC₃₋₆cycloalkyl;
R⁸ is selected from the group consisting of —H, —C₁₋₆ alkyl optionally substituted with 1-3 fluoro, and —C₃₋₆ cycloalkyl optionally substituted with 1-3 fluoro; and
R⁹ is selected from the group consisting of —CH₃ and —F.

2. The compound of claim 1 wherein:
R¹ is

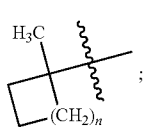

R² is selected from the group consisting of (a) —C₁₋₆alkyl optionally substituted with 1-3 fluoro, (b) —C₃₋₆ cycloalkyl and

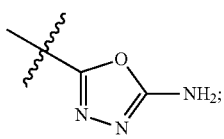 [SMILES: *c1nnc(N)o1]

n is an integer selected from 0, 1, 2 and 3;
R³ is selected from the group consisting of —H, —F, —OH, —CH₃ and —CF₃;
R⁴ is selected from the group consisting of —H and —C₁₋₄alkyl; and
R⁵ is selected from the group consisting of —H and —CH₃.

3. The compound of claim 2 wherein R² is —C₁₋₆alkyl optionally substituted with 1-3 fluoro.

4. The compound of claim 2 wherein R² is selected from —C₃₋₆ cycloalkyl and

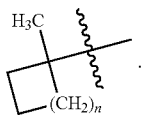

5. The compound of claim 3 wherein R³ is selected from —H, —OH and methyl.

6. The compound of claim 5 wherein R⁴ is selected from —H, methyl and ethyl.

7. The compound of claim 1 selected from the group consisting of those of the following structural formula wherein R², R³, R⁴ and R⁵ are defined as follows:

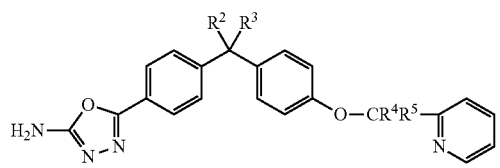

| R² | R³ | R⁴ | R⁵ |
|---|---|---|---|
| t-Bu | H | H | H |
| Me | H | H | H |
| Et | H | H | H |
| Pr | H | H | H |
| i-Pr | H | H | H |
| Cyclopropyl | H | H | H |
| Cyclobutyl | H | H | H |
| Cyclopentyl | H | H | H |
| Cyclohexyl | H | H | H |
|  | H | H | H |
|  | H | H | H |
| Me | Me | H | H |
| Et | Me | H | H |
| i-Pr | Me | H | H |
| t-Bu | Me | H | H |
| Cyclopropyl | Me | H | H |
| Cyclobutyl | Me | H | H |
|  | Me | H | H |

-continued

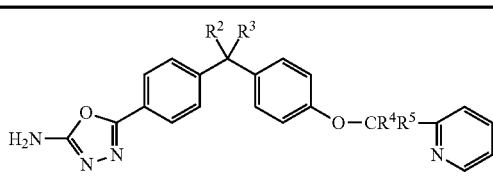

| R² | R³ | R⁴ | R⁵ |
|---|---|---|---|
| 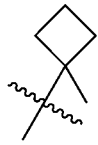 | Me | H | H |
| t-Bu | H | Et | H |
| i-Pr | H | Et | H |
| Cyclopropyl | H | Et | H |
| Cyclobutyl | H | Et | H |
| 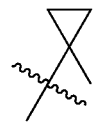 [SMILES: *C1(C)CC1] | H | Et | H |
| 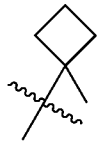 | H | Et | H |
| i-Pr | Me | Et | H |
| t-Bu | Me | Et | H |
| i-Pr | H | Me | H |
| t-Bu | H | Me | H |
| Cyclopropyl | H | Me | H |
| Cyclobutyl | H | Me | H |
| 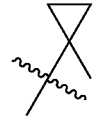 | H | Me | H |
| 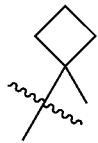 | H | Me | H |
| i-Pr | Me | Me | H |
| t-Bu | Me | Me | H |
| t-Bu | H | Me | Me |

-continued

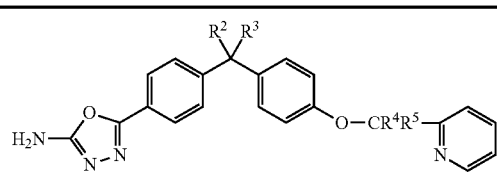

| R² | R³ | R⁴ | R⁵ |
|---|---|---|---|
| i-Pr | H | Me | Me |
| t-Bu | H | Me | Me |
| Cyclopropyl | H | Me | Me |
| Cyclobutyl | H | Me | Me |
| 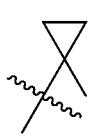 | H | Me | Me |
| 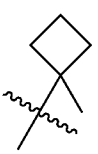 [SMILES: *C1(C)CCC1] | H | Me | Me |
| t-Bu | Me | Me | Me | the pyridyl-N-oxide analogs thereof, or a pharmaceutically acceptable salt thereof.

8. The compound of claim 1 selected from the group consisting of:
5-(4-{2,2-dimethyl-1-[4-(pyridin-2-ylmethoxy)phenyl]propyl}phenyl)-1,3,4-oxadiazol-2-amine;
5-(4-{cyclopropyl[4-(pyridin-2-ylmethoxy)phenyl]methyl}phenyl)-1,3,4-oxadiazol-2-amine;
5-(4-{cyclobutyl[4-(pyridin-2-ylmethoxy)phenyl]methyl}phenyl)-1,3,4-oxadiazol-2-amine;
5-(4-{(1-methylcyclopropyl)[4-(pyridin-2-ylmethoxy)phenyl]methyl}phenyl)-1,3,4-oxadiazol-2-amine;
5-(4-{(1-methylcyclobutyl)[4-(pyridin-2-ylmethoxy)phenyl]methyl}phenyl)-1,3,4-oxadiazol-2-amine;
5-(4-{1,2-dimethyl-1-[4-(pyridin-2-ylmethoxy)phenyl]propyl}phenyl)-1,3,4-oxadiazol-2-amine;
5-(4-{2,2-dimethyl-1-[4-(1-pyridin-2-ylpropoxy)phenyl]propyl}phenyl)-1,3,4-oxadiazol-2-amine;
5-(4-{2,2-dimethyl-1-[4-(1-methyl-1-pyridin-2-ylethoxy)phenyl]propyl}phenyl)-1,3,4-oxadiazol-2-amine; and
the pyridyl-N-oxide analogs thereof; or a pharmaceutically acceptable salt thereof.

9. A pharmaceutical composition comprising a therapeutically effective amount of a compound of claim 1 and a pharmaceutically acceptable carrier.

* * * * *